United States Patent [19]
Uchida et al.

[11] Patent Number: 5,986,121
[45] Date of Patent: Nov. 16, 1999

[54] SILACYCLOPENTADIENE DERIVATIVES AND AN ORGANIC ELECTROLUMINESCENT ELEMENT OBTAINED BY USING THE SILACYCLOPENTADIENE DERIVATIVE

[75] Inventors: Manabu Uchida; Takenori Izumizawa; Kenji Furukawa, all of Kanagawaken; Kohei Tamao; Shigehiro Yamaguchi, both of Kyotofu, all of Japan

[73] Assignee: Chisso Corporation, Osaka, Japan

[21] Appl. No.: 08/678,936

[22] Filed: Jul. 12, 1996

[30] Foreign Application Priority Data

Jul. 17, 1995 [JP] Japan .................................. 7-203763
Jan. 12, 1996 [JP] Japan .................................. 8-021845

[51] Int. Cl.$^6$ ...................................................... C07F 9/02
[52] U.S. Cl. ........................ 556/404; 556/406; 556/465; 556/476; 556/477
[58] Field of Search .................................. 556/406, 404, 556/465, 476, 477

[56] References Cited

FOREIGN PATENT DOCUMENTS

| | | |
|---|---|---|
| 25 34 713 | 8/1975 | Germany . |
| 4442050A1 | 5/1996 | Germany . |
| 63-264692 | 11/1988 | Japan . |
| 4-212286 | 8/1992 | Japan . |
| 4-363891 | 12/1992 | Japan . |
| 5-152072 | 6/1993 | Japan . |
| 5-202011 | 8/1993 | Japan . |
| 5-343184 | 12/1993 | Japan . |
| 6-92947 | 4/1994 | Japan . |
| 6-124784 | 5/1994 | Japan . |
| 6-136359 | 5/1994 | Japan . |
| 6-145658 | 5/1994 | Japan . |
| 6-166746 | 6/1994 | Japan . |
| 6-207169 | 7/1994 | Japan . |
| 6-234968 | 8/1994 | Japan . |
| 6-325871 | 11/1994 | Japan . |
| 7-11244 | 1/1995 | Japan . |
| 7-179477 | 7/1995 | Japan . |

OTHER PUBLICATIONS

T. Izumizawan et al., *Study on Electroluminescent Behaviors of Metal (III) –Quinolinolates.*, 1992 pp. 43–48.

M. Matsuura et al., "*Characteristics of Blue Organic El Devices with Distyrlderivatives .*"

Yuji Hamada et al., "*Oxadiazole Derivatives for Emitter and Carrier Transport Materials in Organic Electroluminescent Devices .*" 1991, pp. 1540–1548.

Junji Kido et al., "*1,2,4, –Triazole Derivative as an Electron Transport Layer in Organic Electroluminescent Devices* ". Jul. 1, 1993, pp. L917–L920.

Takakazu Yamamoto et al., "*Polymer Light–Emitting Diodes with Single–and Double Layer Structures Using Poly (2,3–diphenylquinoxaline–5,8–diyl.)* "Feb. 15, 1994, pp. L250–L253.

Chihaya Adachi et al., "*Organic Electroluminescent Device with a Three–Layer Structure.* " Apr. 4, 1988., L713–L715.

Junji Kido et al., "*Multilayer White Light–Emitting Organic Electroluminescent Device .*" Mar. 3, 1995., pp. 1332–1334.

Chihaya Adachi et al., "*Electroluminescence in Organic Films with Three–Layer Structure .*"

C.W. Tang et al. "*Electroluminescence of Doped Organic Thin Films .*" Jan. 4, 1989., pp. 3610–3616.

Chihaya Adachi et al., "*Organic Electroluminescent Device Having a Hole Conductor as an Emitting Layer .*" Jul. 31, 1989., pp. 1489–1491.

Krauder et al., "*Preparation of heterospiro compounds of main Group 4 elements as electroluminescence material* ", Chemical Abstracts, No. 125:114858r, vol. 125, No. 9, 1996.

*Primary Examiner*—John M. Cooney, Jr.
*Attorney, Agent, or Firm*—McDermott, Will & Emery

[57] ABSTRACT

An electroluminescence element (EL) obtained by using a silacyclopentadiene. derivation expressed by the general formula (I) and the derivative are provided.

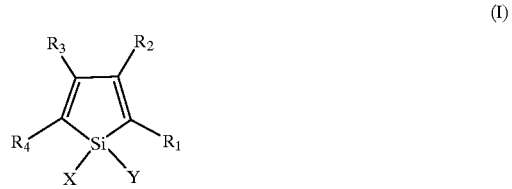

(I)

(wherein X and Y are independently hydrocarbon radicals with from 1 to 6 atoms and $R_1$ to $R_4$ are hydrogen, halogens, alkyl radicals with from 1 to 6 carbon atoms, or a condensed (un)substituted ring if being adjacent).

12 Claims, No Drawings

SILACYCLOPENTADIENE DERIVATIVES AND AN ORGANIC ELECTROLUMINESCENT ELEMENT OBTAINED BY USING THE SILACYCLOPENTADIENE DERIVATIVE

BACKGROUND OF THE INVENTION

The present invention relates to a silacyclopentadiene derivative. In more detail, the invention relates to a silacyclopentadiene derivative and an electroluminescent (EL) element using said derivative.

Recently, organic EL elements have been noticed as candidates for plain displays having such a high luminance which has never been obtained, so that studies and developments thereof have been activated. The organic EL element has such a structure that an organic luminescent layer being sandwiched by two electrodes, and it emits luminescence by recombination of holes injected from an anode and electrons injected from a cathode in a luminescent layer. The organic materials used for the said organic EL elements include low molecular weight materials and polymer materials, both of which can make EL elements with high luminance. There are two types in such organic EL elements. One type is an element having a fluorescent dye doped in an electron-transporting layer which has been published by C. W. Tang and et al (J. Appl. Phys.), 65, 3610 (1989)), and the other type is an element having a fluorescent dye singly used (such as an element described in Jpn. J. Appl. Phys., 27, L269 (1988)). In the latter element, it was shown that a luminous efficiency was improved in the case of a fluorescent dye being laminated with a hole-carrying layer for only carrying holes, which are one of electric charges, and/or with an electron-carrying layer for carrying only electron. Although many various materials such as triphenylamine derivatives are known as hole-transporting materials used for organic EL elements, there are a few electron-transporting. Furthermore, the known electron-transporting materials have lower charge carrier transporting abilities than the known hole-transporting materials such as N,N'-diphenyl-N,N'-di(3-methylphenyl)-4,4'-diarninobiphenyl (TPD), and in the case of being used for organic EL elements, ability thereof can not cause sufficient elemental characteristics because of limitation by the used electron-transporting materials.

As examples of such electron-transporting materials, metal complexes of oxine derivatives (Denshi Joho Tsushin Gakkai Gijutsu Kenlyu Hokoku, 92(311), 43(1992)) and 2-(4-biphenylyl)-5-(4-tert-butylphenyl)-1,3,4-oxadiazole (PBD) etc. have been known. The former can operate organic EL elements at a relatively low voltage, but insufficiently, and it is difficult to obtain blue luminance due to the own green luminance. As examples of the latter used as electron-transporting layers, there have been organic EL elements described in the above-mentioned Jpn. J. Appl. Phys., 27, L269 (1988). It was, however, pointed out that stability of the thin film is poor due to a tendency of crystallization about the said described organic EL elements, and then compounds having multiple oxadiazole rings have been developed (such as those described in Nippon Kagakukai-shi, 11, 1540 (1991), Toku-Kai-Hei 6-145658, Toku-Kai-Hei 6-92947, Toku-Kai-Hei 5-152072, Toku-Kai-Hei 5-202011, and Toku-Kai-Hei 6-136359 etc.). They however have not sufficient properties for practical uses such as high operative voltage. As an another compound type, quinoxaline derivatives have been reported (Toku-Kai-Hei 6-207169). Although stabilities of the thin films are improved by dimerizing quinoxaline to increase their molecular weights, they are insufficient for practical uses because of high operative voltage.

As characteristics of the electron-transporting materials used for the said organic EL elements, superiority in electron-carrying ability is necessary first.

On one hand, there have been mentioned those disclosed in Toku-Kai-Hei 7-179477 official gazette as recent reported examples of the silacyclopentadiene derivatives, but they related to reactive intermediates with intention of application to π-electron conjugated type organic polymers, not to the organic EL elements according to this invention. Furthermore, examples of copolymers with thiophene have been disclosed in Toku-Kai-Hei 6-166746 official gazette, but these compounds are unsuitable as electron-transporting materials for organic EL elements because of long absorption wavelength and luminous wavelength.

Furthermore, there were examples of silane derivatives utilized for organic EL elements in Toku-Kai-Hei 6-325871 official gazette, but those having silacyclopentadiene rings were not shown amongst the disclosed organic silicone compounds therein, and also the said derivatives are low in electron-carrying property, there being not described any usefulness as electron-transporting materials.

Furthermore, there were examples of silane derivatives utilized for organic EL elements in Toku-Kai-Hei 5-343184, Toku-Toku-Kai-Hei 6-124784, Toku-Kai-Hei 6-234968, Toku-Kai-Hei 6-293778 and Toku-Kai-Hei 7-11244 official gazettes, but silacyclopentadiene rings were not included in the disclosed organic silane compounds therein, and also there has not any description about an electron-transporting property and the practical use examples were only as interfacial layers for improvement in adhesively between hole-transporting materials or luminescent layers and anodes, so that there was no description as electron-transporting materials.

The present inventors had studied zealously in order to solve these problems and to find organic EL elements with low voltage and high luminous efficiency. As a result, it was found that silacyclopentadiene derivatives to be used for organic EL elements can solve the above-mentioned problems to complete the present invention.

As clear from the above description, an object of the invention is to provide organic EL elements by which high luminant emission can be obtained at low voltage.

SUMMARY OF THE INVENTION

The present invention has the constitution of the following items (1), (2), (3), (4), (5), (6), (7), (8), (9), (10), (11), (12), (13), (14), (15), (16) and (17).

(1) A silacyclopentadiene derivative expressed by the following formula I

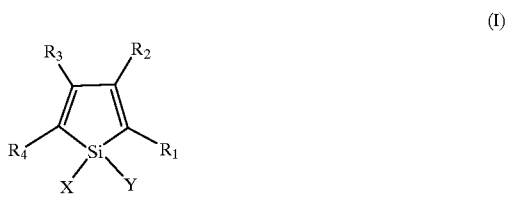

(I)

(wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated ring, and from $R_1$ to $R_4$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, heterocyclic radicals, alkenyl radicals, nitro radical, formyl radical, nitroso radical, formyloxy radical, isocyano radical, cyanate radical, isocyanate radical, thiocyanate radical, isothiocyanate radical or cyano radical, or they may form a structure of a substituted or unsubstituted condensed ring if they are adjacent, with the proviso that in the case of $R_1$ and $R_4$ being phenyl radicals, X and Y are not alkyl radicals and phenyl radicals; in the case of $R_1$ and $R_4$ being thienyl radicals, X and Y are not monovalent hydrocarbons simultaneousy, and $R_2$ and $R_3$ are not alkyl radicals, aryl radicals or alkenyl radicals or $R_2$ and $R_3$ are not aliphatic radicals to form a ring simultaneously; in the case of $R_1$ and $R_4$ being silyl radicals, $R_2$, $R_3$, X and Y are independent each other and are not monovalent hydrocarbon radicals with from 1 to 6 carbon atoms or hydrogen atom; and in the case of $R_1$ and $R_2$ being condensed to form a benzene ring, X and Y are not alkyl radicals and phenyl radicals).

(2) A silacyclopentadiene derivative expressed by the following formula II

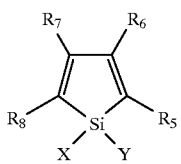

(II)

(wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated ring, and from $R_5$ to $R_8$ denote independently each other hydrogen, fluorine, chlorine, substituted or unsubstituted alkyl radicals with from 1 to 6 carbon atoms, alkoxy radicals, perfluoroalkyl radicals, perfluoroalkoxy radicals, dialkylamino radicals, diacylamino radicals, silyl radical, aryl radicals, heterocyclic radicals or cyano radical, or they may form a structure of a substituted or unsubstituted condensed ring if they are adjacent, with the proviso that in the case of $R_5$ and $R_8$ being phenyl radicals, X and Y are not alkyl radicals and phenyl radicals; in the case of $R_5$ and $R_8$ being thienyl radicals, X and Y are not monovalent hydrocarbons simultaneousy, and $R_6$ and $R_7$ are not alkyl radicals, aryl radicals or alkenyl radicals or $R_6$ and $R_7$ are not aliphatic radicals to form a ring simultaneously; in the case of $R_5$ and $R_8$ being silyl radicals, $R_6$, $R_7$, X and Y are independent each other and are not monovalent hydrocarbon radicals with from 1 to 6 carbon atoms or hydrogen atom; and in the case of $R_5$ and $R_6$ being condensed to form a benzene ring, X and Y are not akyl radicals and phenyl radicals and halogens).

(3) A silacyclopentadiene derivative expressed by the following formula III

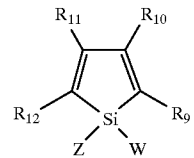

(III)

(wherein, Z and W denote independently each other saturated or unsaturated hydrocarbon radicals with from 1 to 6 carbon atoms, substituted or unsubstituted aryl radicals or substituted or unsubstituted heterocycles, or Z and W are bonded together to form a structure of a saturated ring, and from $R_9$ to $R_{12}$ denote independently each other substituted or unsubstituted alkyl radicals with from 1 to 6 carbon atoms, perfluoroalkyl radicals, diacylamino radicals, silyl radical, aryl radicals or heterocyclic radicals, or they may form a structure of a substituted or unsubstituted condensed ring if they are adjacent, with the proviso that in the case of $R_9$ and $R_{12}$ being phenyl radicals, Z and W are not allyl radicals and phenyl radicals; in the case of $R_9$ and $R_{12}$ being thienyl radicals, Z and W are not monovalent hydrocarbons simultaneousy, and $R_{10}$ and $R_{11}$ are not alkyl radicals or aryl radicals or $R_{10}$ and $R_{11}$ are not aliphatic radicals to form a ring simultaneously; in the case of $R_9$ and $R_{12}$ being silyl radicals, $R_{10}$, $R_{11}$, Z and W are independent each other and are not monovalent hydrocarbon radicals with from 1 to 6 carbon atoms or hydrogen atom; and in the case of $R_9$ and $R_{10}$ being condensed to form a benzene ring, Z and W are not alkyl radicals and phenyl radicals).

(4) A silacyclopentadiene derivative expressed by the following formula IV

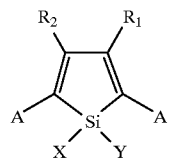

(IV)

(wherein, A denotes a zinc halide or a zinc halide complex, X and Y denote independently each other saturated or unsaturated hydrocarbon radicals with from 1 to 6 carbon atoms, alkoxy radicals, alkenyloxy radicals, allcynyloxy radicals, substituted or unsubstituted aryl radicals or substituted or unsubstituted heterocycles, or X and Y are bonded together to form a structure of a saturated or unsaturated ring, and $R_1$ and $R_2$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, heterocyclic radicals, alkenyl radicals, alkynyl radicals, nitro radical, formyl radical, nitroso radical, formyloxy radical, isocyano radical, cyanate radical, isocyanate radical, thiocyanate radical, isothiocyanate radical or cyano radical, or a structure of a substituted or unsubstituted condensed ring).

(5) A silacyclopentadiene derivative expressed by the following formula (V)

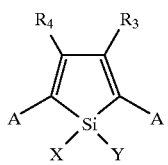

(V)

(wherein, A denotes a zinc halide or a zinc halide complex, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_3$ and $R_4$ denote independently each other hydrogen, fluorine, chlorine, substituted or unsubstituted allyl radicals with from 1 to 6 carbon atoms, alkoxy radicals, perfluoroalkyl radicals, perfluoroalkoxy radicals, dialkylamino radicals, diarylamino radicals, silyl radical, aryl radicals, heterocyclic radicals or cyano radical, or they may form a structure of a substituted or unsubstituted condensed ring).

(6) A silacyclopentadiene derivative expressed by the following formula VI

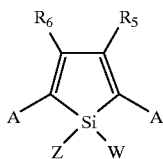

(VI)

(wherein, A denotes a zinc halide or a zinc halide complex, X and Y denote independently each other saturated or unsaturated hydrocarbon radicals with from 1 to 6 carbon atoms, substituted or unsubstituted aryl radicals or substituted or unsubstituted heterocycles, or X and Y are bonded together to form a structure of a saturated or unsaturated ring, and from $R_5$ and $R_6$ denote independently each other substituted or unsubstituted alkyl radicals with from 1 to 6 carbon atoms, perfluoroalkyl radicals, diarylamino radicals, silyl radical aryl radicals or heterocyclic radicals, or they may form a structure of a substituted or unsubstituted condensed ring).

(7) A process for preparing a silacyclopentadiene derivative according to the above-mentioned item 4, characterized in that an acetylene derivative expressed by the following formula VII

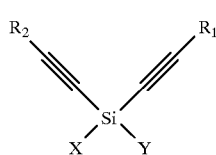

(VII)

(wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_1$ and $R_2$ denote independently each other hydrogen, halogens, substituted or unsubstituted aklyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, heterocyclic radicals, alkenyl radicals, alkynyl radicals, nitro radical, formyl radical, nitroso radical, formyloxy radical, isocyano radical, cyanate radical, isocyanate radical, thiocyanate radical, isothiocyanate radical, cyano radical, or a structure of a substituted or unsubstituted condensed ring) is reacted with an alkali metal complex, then with a silane derivative expressed by the following formula VIII:

(VIII)

(wherein, X Y and Z denote independently tertiary butyl radicals or aryl radicals), and thereafter with zinc chloride or a zinc chloride complex.

(8) A process for preparing a silacyclopentadiene derivative according to the above-mentioned item 5, characterized in that an acetylene derivative expressed by the following formula IX:

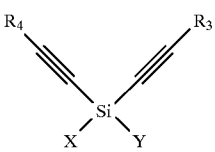

(IX)

(wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_3$ and $R_4$ denote independently each other hydrogen, fluorine, chlorine, substituted or unsubstituted alkyl radicals with from 1 to 6 carbon atoms, alkoxy radicals, perfluoroalkyl radicals, perfluoroalkoxy radicals, dialkylamino radicals, diarylamino radicals, silyl radical aryl radicals, heterocyclic radicals, cyano radical or a structure of a substituted or unsubstituted condensed ring) is reacted with an alkali metal complex, then with a silane derivative expressed by the following formula X:

(X)

(wherein, X Y and Z denote independently tertiary butyl radicals or aryl radicals), and thereafter furthermore with zinc chloride or a zinc chloride complex.

(9) A process for preparing a silacyclopentadiene derivative according to the above-mentioned item 6, characterized in that an acetylene derivative expressed by the following formula XI:

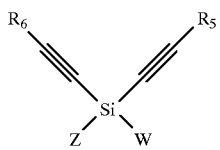

(XI)

(wherein, A denotes a zinc halide or a zinc halide complex, X and Y denote independently each other saturated or unsaturated hydrocarbon radicals with from 1 to 6 carbon atoms, substituted or unsubstituted aryl radicals or substituted or unsubstituted heterocycles, or X and Y are bonded together to form a structure of a saturated or unsaturated ring, and from $R_5$ and $R_6$ denote independently each other substituted or unsubstituted alkyl radicals with from 1 to 6 carbon atoms, perfluoroalkyl radicals, diarylamino radicals, silyl radical, aryl radicals or heterocyclic radicals, or they may form a structure of a substituted or unsubstituted condensed ring) is reacted with an alkali metal complex, then with a silane derivative expressed by the following formula X:

(X)

(wherein, X, Y and Z denote independently tertiary butyl radicals or aryl radicals), and thereafter furthermore with zinc chloride or a zinc chloride complex.

(10) A process for preparing a silacyclopentadiene derivative, characterized in that a silacyclopentadiene derivative according to the above-mentioned item 7 is reacted with a halide expressed by the following formula (XII):

LX        (XII)

(wherein, X represents chlorine, bromine or iodine, and L denotes a halogen, a saturated or unsaturated hydrocarbon radical with from 1 to 6 carbon atoms, a perfluoroalkyl radical, an alkylcarbonyl radical, an arylcarbonyl radical, an alkoxycarbonyl radical, an aryloxy carbonyl radical, a sulfinyl radical, a sulfonyl radical, a sulfanil radical, a silyl radical, an aryl radical, a heterocyclic radical, an alkenyl radical or an alkynyl radical).

(11) A process for preparing a silacyclopentadiene derivative, characterized in that a silacyclopentadiene derivative according to the above-mentioned item 8 is reacted with a halide expressed by the following formula XII:

MX        (XIII)

(wherein, X represents chlorine, bromine or iodine, and M denotes fluorine, chlorine, a saturated or unsaturated hydrocarbon radical with from 1 to 6 carbon atoms, a perfluoroalkyl radical, a silyl radical, an aryl radical or a heterocyclic radical).

(12) A process for preparing a silacyclopentadiene derivative, characterized in that a silacyclopentadiene derivative according to the above-mentioned item 9 is reacted with a halide expressed by the following formula XIV:

NX        (XIV)

(wherein, X represents chlorine, bromine or iodine, and N denotes a saturated or unsaturated hydrocarbon radical with from 1 to 6 carbon atoms, a perfluoroalkyl radical, a silyl radical, an aryl radical or a heterocyclic radical).

(13) An electroluminescent element obtained by using a silacyclopentadiene derivative expressed by the formula XV

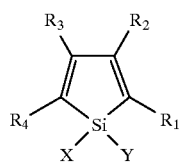

(XV)

(wherein, X and Y denote independently each other saturated or unsaturated hydrocarbon radicals with from 1 to 6 carbon atoms, alkoxy radicals, alkenyloxy radicals, alkcynyloxy radicals, hydroxy radical, substituted or unsubstituted aryl radicals, or substituted or unsubstituted heterocycles, or X and Y are bonded together to form a structure of a saturated or unsaturated ring, and from $R_1$ to $R_4$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical alkylcarbonyloxy radicals, arylcarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, hetrocyclic radicals, alkenyl radicals, alkynyl radicals, nitro radical, formyl radical, nitroso radical, formyloxy radical, isocyano radical, cyanate radical, isocyanate radical, thiocyanate radical, isothiocyanate radical or cyano radical or substituted or unsubstituted condensed rings in the case of being adjacent).

(14) An electroluminescent element characterized in that at least one silacyclopentadiene derivative according to the above-mentioned item 13 is used as a component of an electron-transporting layer.

(15) An electroluminescent element characterized in that at least one silacyclopentadiene derivative according to the above-mentioned item 13 is used as a component of a luminescent layer.

(16) An electroluminescent element characterized in that at least one silacyclopentadiene derivative according to the above-mentioned item 13 is used as a component of a hole-obstructing layer.

(17) An electroluminescent element characterized in that a silacyclopentadiene derivative expressed by the formula XVI

XVI

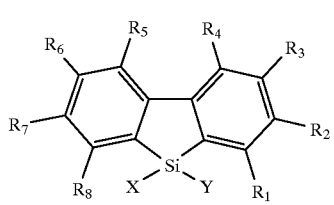

(wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals, or substituted or unsubstituted heterocycles, and from $R_1$ to $R_4$ denote independently each other hydrogen, halogens, substituted or unsubstituted alkyl radicals with from 1 to 6 carbon atoms, alkoxy radicals, perfluoroalkyl radicals, perfluoroalkoxy radicals, amino radical, alkylcarbonyl radicals, alkoxycarbonyl radicals, formyl radical, nitroso radical, azo radical, alkylcarbonyloxy radicals, alkoxycarbonyloxy radicals, formyloxy radicals, sulfinyl radical, sulfonyl radical, sulfanil radical, silyl radical, isocyano radical, carbamoyl radical, cyanate radical, isocyanate radical, thiocyanate radical, isothiocyanate radical, aryl radicals, alkenyl radicals, alkynyl radicals or cyano radical or substituted or unsubstituted condensed rings in the case of being adjacent) is used as a component of a hole-obstructing layer.

DETAILED DESCRIPTION OF THE INVENTION

Silacyclopentadiene derivatives according to the invention can be obtained for example by the following preparation method. That is, the acetylene derivative expressed by the above-mentioned Formula VII is reacted with an alkali metal complex, then treated with the silane derivative expressed by the above-mentioned Formula VIII, and thereafter reacted with zinc chloride or a zinc chloride complex, to obtain the reactive silacyclopentadiene derivative expressed by the above-mentioned Formula IV. As the substituents for the acetylene derivatives to be used, those difficulty obstructing the reaction of the alkali metal complex and acetylene are suitable, and those being inert to the alkali metal complex are more preferable. As alkali metal complexes, there may be mentioned lithium naphthalenide, sodium naphthalenide, potassium naphthalenide, lithium 4,4'-ditertiary-butyl-2,2'-biphenylide or lithium (N,N-dimethylamino) naphthalenide etc. As solvents to be used, there is not any particular limitation if they are inert to alkali metals or alkali metal complexes, and ether type solvents such as diethyl ether or tetrahydrofuran etc. are generally preferable. As substituents for the silane derivatives to be used then, they are preferably bulky one, and tertiary-butyl diphenyl chlorosilane or ditertiary-butyl phenyl chlorosilane may be mentioned as examples thereof. By adding the said silane derivative, the subsequent reaction may be possibly proceeded smoothly, so that silacyclopentadiene derivative according to the invention can be obtained with high yield in one step.

As zinc chloride or zinc chloride complexes, solid zinc chloride directly, an ether solution of zinc chloride, or tetramethylethylenediantine complex of zinc chloride etc. may be mentioned. These zinc chlorides are preferably dried sufficiently, and if moisture being much, it is difficult to obtain the objective substance. It is preferable to carry out this reaction in an inert gas flow, and argon gas etc. may be used as the said inert gas. But, after addition of the silane derivative, there is not any problem even under a nitrogen atmosphere.

The silacyclopentadiene derivative according to the invention can be obtained by reacting the obtained reactive silacyclopentadiene derivative with the halide expressed by the above-mentioned Formula XII in the presence of a catalyst. As catalysts used herein, there may be mentioned palladium catalysts such as tetrakistriphenylphosphine palladium or dichlorobistriphenylphosphine palladium etc. In each steps of the subsequent reactions, there is not any particular limitation as to the reaction temperatures, but it is preferably below the room temperature, generally below 0° C., for adding and stirring the silane derivative and zinc chloride etc. The reaction temperature after addition of the halide, it is preferably above the room temperature, generally under reflux in the case of tetrahydrofuran being used as the solvent. There is not any particular limitation as to the reaction time, and it is desirably from several minutes to several hours in the case of adding and stirring the alkali metal complex, the silane derivative and zinc chloride etc. Reactions after addition of the halide may be monitored by general analytical methods such as NMR or chromatography etc. to determine the ends of the reactions.

In the case that a benzene ring being condensed with a silacyclopentadiene ring in the formula according to the invention, a method which is different from the above-mentioned preparation method is used. There is not any particular limitation as to the method if it being known, and there may be mentioned the following method. That is, the silacyclopentadiene derivative according to the invention can be obtained by re-acting an alkali metal, an alkali earth metal or an alkali metal complex to a 2,2'-dihalogenobiphenyl derivative expressed by the following Formula XVII:

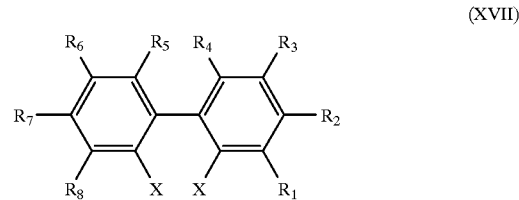

(XVII)

(wherein, X expressed chlorine, bromine or iodine, and from $R_1$ to $R_8$ are saturated or unsaturated hydrocarbon radicals with from 1 to 6 carbon atoms, alkoxy radicals, alkenyloxy radicals, alkynyloxy radicals, fluorine, hydrogen, substituted or unsubstituted aryl radicals, substituted or unsubstituted heterocycles, cyano radical or structures of saturated or unsaturated rings if being adjacent), and reacting thereto a dichlorosilane derivative expressed by the following Formula XVIII:

(XVIII)

(wherein, X and Y are independently each other saturated or unsaturated hydrocarbon radicals with from 1 to 6 carbon atoms, alkoxy radicals, alkenyloxy radicals, alkynyloxy radicals, substituted or unsubstituted aryl radicals, or substituted or unsubstituted heterocycles, or X and Y are bonded together to form a structure of saturated or unsaturated ring).

As metals used herein, there may be mentioned lithium, magnesium, sodium or potassium etc., and as metal complexes, there may be mentioned normal-butyl lithium or phenyl lithium etc. As substituents for 2,2'-dihalogenobiphenyl derivatives expressed by the above-mentioned Formula XVI, there is not any particular limitation if it being inert to alkali metals, alkali earth metals or alkali metal complexes under the reaction conditions.

There is not any particular limitation as to the reaction temperature when alkali metals, alkali earth metals or alkali metal complexes being reacted. But, when highly reactive substituents such as cyano radical being present, low temperature is preferable and generally below −70° C. As reaction solvents to be used, there is not any particular limitation if being inert to alkali metals, alkali earth metals or alkali metal complexes.

As substituents bonded to silicons of the thus obtained silacyclopentadiene derivatives according to the invention, there may be mentioned alkyl radicals such as methyl radical, ethyl radical, normal-propyl radical, isopropyl radical, cyclopentyl radical or tertiary-butyl radical; alkenyl radicals such as vinyl radical, allyl radical, butenyl radical or styryl radical; alkynyl radicals such as ethynyl radical, propargyl radical or phenylacetynyl radical; alkoxy radicals such as methoxy radical, ethoxy radical, isopropoxy radical or tertiary-butoxy radical; alkenyloxy radicals such as vinyloxy radical or allyloxy radical; alkynyloxy radicals such as ethynyloxy radical or phenylacetyloxy radical; aryl radicals such as phenyl radical, naphthyl radical, anthracenyl radical, biphenyl radical, toluyl radical, pyrenyl radical, perylenyl radical, anisyl radical, terphenyl radical or phenanthrenyl radical; heterocycles such as hydropyrenl radical, hydropyrenyl radical, dioxanyl radical, thienyl radical, furyl radical, oxazolyl radical, oxadiazolyl radical, thiazolyl radical, thiadiazolyl radical, acrydinyl radical, quinolyl radical, quinoxaloyl radical, phenanthrolyl radical, benzothienyl radical, benzothiazolyl radical, indolyl radical, silacyclopentadienyl radical or pyridyl radical etc.

Furthermore, these substituents may be bonded at optional sites each other to form a ring. As substituents bonded to carbon atoms of silacyclopentadiene ring, there may be mentioned hydrogen; halogens such as fluorine or chlorine; alkyl radicals such as methyl radical, ethyl radical, normal-propyl radical, isopropyl radical, cyclopentyl radical or tertiary-butyl radical; alkenyl radicals such as vinyl radical, allyl radical, butenyl radical or styryl radical; alkynyl radicals such as ethynyl radical, propargyl radical or phenylacetynyl radical; alkoxy radicals such as methoxy radical, ethoxy radical, isopropoxy radical or tertiary-butoxy radical; alkenyloxy radicals such as vinyloxy radical or allyloxy radical; alkynyloxy radicals such as ethynyloxy radical or phenylacetyloxy radical; aryloxy radicals such as phenoxy radical, naphthoxy radical, biphenyloxy or pyrenyloxy radical; perfluoro radicals such as trifluoromethyl radical, trifluoromethoxy radical or pentafluoroethoxy radical; amino radicals such as dimethylamino radical, diethylamino radical or diphenylamino radical; ketone radicals such as acetyl radical or benzoyl radical; ester radicals such as acetoxy radical or benzoyloxy radical; ester radicals such as methoxycarbonyl radical, ethoxycarbonyl radical or phenoxycarbonyl radical; sulfinyl radicals such as methylsulfinyl radical or phenylsulfinyl radical; silyl radicals such as trimethylsilyl radical, dimethyltertiary-butylsilyl radical, trimethoxysilyl radical or triphenylsilyl radical; aryl radicals such as phenyl radical, biphenyl radical, terphenyl radical, naphthyl radical, anthracenyl radical, pyrenyl radical, toluyl radical, anisyl radical, fluorophenyl radical, diphenylaminophenyl radical, dimethylaminophenyl radical, diethylaminophenyl radical or phenanthrenyl radical; heterocycles such as thienyl radical, furyl radical, silacyclopentadienyl radical, oxazolyl radical, oxadiazolyl radical, thiazolyl radical, thiadiazolyl radical, acrydinyl radical, quinolyl radical, quinoxaloyl radical, phenanthrolyl radical, benzothienyl radical, benzothiazolyl radical, indolyl radical, carbazolyl radical, pyridyl radical, pyrolyl radical, benzoxazolyl radical, pyrimidyl radical or imidazolyl radical etc.; nitro radical; formyl radical; nitroso radical, formyloxy radical; isocyano radical; cyanate radical; isocyanate radical; thiocyanate radical; isothiocyanate radical or cyano radical etc.

Furthermore, these substituents may be bonded at optional sites each other to form a ring. Methods for introducing these substituents may be introduction before forming of silacyclopentadiene ring, or may be introduction after forming of silacyclopentadiene ring. Silacyclopentadiene derivatives according to the invention are effective as electron-carrying materials for organic EL elements, and it is found by means of an ab-initio calculation that silacyclopentadiene ring has at lowest unoccupied molecular orbital and has a more receptive structure for electrons than corresponding cyclopentadiene ring, thiophene ring, pyrrole ring or furan ring. This is considered to be caused by interaction between $\pi^*$ orbit of diene part and $\sigma^*$ orbit of silicon, but it cannot be decided hastily whether they are superior as electron-carrying materials for organic EL elements or not only by such reasons. The structure of silacyclopentadiene ring may be considered to effect electron-carrying property.

Furthermore, the formulas according to the invention are superior as electron-carrying materials for organic EL elements to the organic silane formulas disclosed in Toku-Kai-Hei 6-325871 official gazette, that is, introduction of silacyclopentadiene ring may be considered to effect much.

As examples of silacyclopentadiene derivatives used in the above item (13) to (17), the following formulas may be mentioned:

1,1-dimethyl-2,3,4,5-tetraphenylsilacyclopentadiene,
1,1-diethyl-2,3,4,5-tetrakis(2-methylphenyl) silacyclopentadiene,
1,1-diisopropyl-2,3,4,5-tetrakis(3-methylphenyl) silacyclopentadiene,
1-ethyl-1-methyl-2,3,4,5-tetrakis(4-methylphenyl) silacyclopentadiene,
1,1-ditertiary-butyl-2,3,4,5-tetrakis(2-ethylphenyl) silacyclopentadiene,
1,1-diphenyl-2,3,4,5-tetrakis(3-ethylphenyl) silacyclopentadiene,
1-methyl-1-phenyl-2,3,4,5-tetrakis(4-ethylphenyl) silacyclopentadiene,
1-phenyl-1-tertiarybutyl-2,3,4,5-tetrakis(3-terdary-butylphenyl)silacyclopentadiene,
1,1-dimethyl-2,5-bis(3-methylphenyl)-3,4-diphenylsilacyclopentadiene,
1,1-di(4-toluyl)-2,5-bis(4-methylphenyl)-3,4diphenylsilacyclopentadiene,
1-silacyclohexane-1-spiro-2',5'-di(2-biphenyl)-3',4'-diphenyl-1'-silacyclopentadiene,
1-silacyclopentane-1-spiro-2',5'-di(3-biphenyl)-3'4'-diphenyl-1'-silacyclopentadiene,
9-silafluorene-9-spiro-2',5'-di(4-biphenyl)-3',4'-diphenyl-1'-silacyclopentadiene,
1,1-dimethyl-2,5-bis(2-trifuoromethylphenyl)-3,4-diphenylsilacyclopentadiene,
1,1 -dimethyl-2,5-bis(3-fluorophenyl)-3,4-diphenylsilacyclopentadiene,
1,2-bis(1-methyl-2,5-bis(3 -methoxyphenyl)-3,4-diphenylsilacyclopentadienyl)ethane,
1,1-dimethyl-2,5-bis(4-cyanophenyl)-3,4-diphenylsilacyclopentadiene,
1,1-dimethyl-2,5-bis{2-(2-benzoxazolyl)phenyl}-3,4-diphenylsflacyclopentadiene,
1,1-dimethyl-2,5-bis{3-(2-benzothienyl)phenyl}-3,4-diphenylsilacyclopentadiene,
1,1-dimethyl-2,5-bis{4-(2-benzoftiryl)phenyl}-3,4-diphenylsilacyclopentadiene,
1,1-dimethyl-2,5-bis{2-(2-benzothiazolyl)phenyl}-3,4diphenylsilacyclopentadiene,
1,1-dimethyl-2,5-bis{3-(2-benzoimidazolyl)phenyl}-3,4-diphenylsilacyclopentadiene,
1,1-dimethyl-2,5-bis{4-(2-indolyl)phenyl}-3,4-diphenylsilacyclopentadiene, 1,1-dimethyl-2,5-bis{3-(5-methoxy-2-benzothiazolyl) phenyl}-3,4-diphenylsilacyclopentadiene,
1,1-dimethyl-2,5-di(1-naphthyl)-3,4-diphenylsilacyclopentadiene,
1,1-dimethyl-2,5-di(2-methyl-1-naphthyl)-3,4-diphenylsilacyclopentadiene,
1,1-dimethoxy-2,5-di(2-naphthyl)-3,4-diphenylsilacyclopentadiene,
1,1-dimethyl-2,5-di(2-benzothienyl)-3,4diphenylsilacyclopentadiene, 1,1-dimethyl-2,5-bis(3-methyl-2-benzothienyl)-3,4-diphenylsilacyclopentadiene,
1,1-dimethyl-2,5-bis(3-phenyl-2-benzothienyl)-3,4-diphenylsflacyclopentadiene,
1,1-dimethyl-2,5-bis(2-methyl-3-benzothienyl)-3,4-diphenylsilacyclopentadiene,
1,1-dimethyl-2,5-di(2-benzothiazolyl)-3,4-diphenylsilacyclopentadiene,
1,1-dimethyl-2,5-di(2-benzoxazolyl)-3,4-diphenylsilacyclopentadiene,
1,1-dimethyl-2,5-bis(5-methyl-2-benzoxazolyl)-3,4-diphenylsilacyclopentadiene,
1,1-dimethyl-2,5-bis(5-phenyl-2-benzothiadiazolyl)-3,4-diphenylsilacyclopentadiene,
1,1-dimethyl-2,5-di(3-benzofuranyl)-3,4-diphenylsilacyclopentadiene,
1,1-dimethyl-2,5-bis(3,4-difluorophenyl)-3,4-diphenylsilacyclopentadiene,
1,1-dimethyl-2,5-bis(3,4,5-trifluorophenyl)-3,4-diphenylsilacyclopentadiene,
1,1-dimethyl-2,5-bis(2,3,4,5,6-pentafluorophenyl)-3,4-diphenylsflacyclopentadiene,
5,5'-dibromo-1,1,1',1'-tetraethyl-3,3',4,4'-tetraphenyl-2,2'-bisilol,
5,5'-dimethyl-1,1,1',1'-tetraethyl-3,3',4,4'-tetraphenyl-2,2'-bisilol,
5,5'''-dibromo-1,1,1',1',1'',1'',1''',1'''-octaethyl-3,3',3'',3''',4,4',4'',4'''-octaphenyl-2,2':5',2'':5'',2'''-quartersilol,
9,9'-silaspirobifluorene,
9,9-diphenyl-9-silafluorene,
9,9-dinaphthyl-9-silafluorene, compounds expressed by Formula XIX (TTSTT)

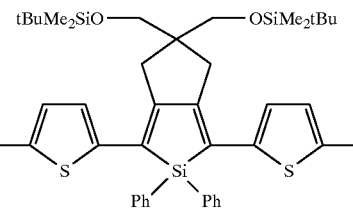

(XIX)

compounds expressed by Formula XX.

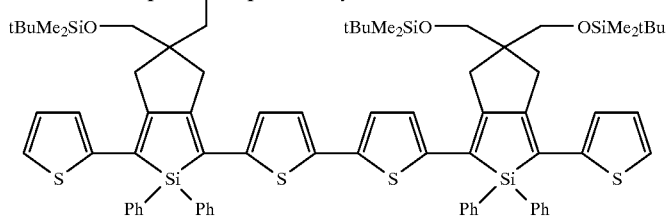

(XX)

Furthermore, these silacyclopentadiene derivatives are useful as luminescent materials for EL elements, since they fluoresce strongly by theirselves. For example, 1,1-dimethyl-2,5-bis(3-fluorophenyl)-3,4-diphenyl silacyclopentadiene fluoresces blue, 1,1-dimethyl-2,5-bis(3-methylphenyl)-3,4-diphenyl silacyclopentadiene fluoresces green, and TTSTT fluoresces red.

Although the constitutions of EL elements according to the invention can take various embodiments, their basic constitutions are to sandwich silacyclopentadiene derivatives between one pair of electrodes (anode and cathode), and if required, hole-transporting materials, luminescent materials and electron-transporting materials may be added or laminated as another layers. For example, there may be mentioned anode/silacyclopentadiene derivative layer/cathode, anode/hole-transporting layer/silacyclopentadiene derivative layer/cathode, anode/hole-transporting layer/luminescent layer/silacyclopentadiene derivative layer/cathode, anode/hole-transporting material+luminescent material+silacyclopentadiene derivative layer/cathode.

In this case, the layer which fluoresces is a hole-transporting layer or silacyclopentadiene derivative layer. As silacyclopentadiene derivatives which have effects of hole-obstruction, those with short luminescent wavelength may be particularly mentioned. For example, 9,9'-silaspirobifluorene is mentioned.

In elements obtained by using the said 9,9'-silaspirobifluorene as an hole-obstruction layer, TPD as a hole-transporting layer, and 8-hydroxyquinoline aluminium (Alq) as an electron-transporting layer, their luminescences may be seen as violet derived from luminescence of TPD and always very superior hole-obstructive ability is obtained.

Although there are elements in which TPD being fluorescent element obtained by using triazole derivatives by Kido (Science, 267, 1332 (1995)), they are incomplete. Furthermore, silacyclopentadiene derivative layers to be used according to the invention can be used as fluorescent layers or electron-transporting luminescent layers in special embodiments. As the constitution of the elements in this case, there may be mentioned anode/hole-transporting layer/(silacyclopentadiene derivative+electron-transporting material) layer/cathod etc.

The elements according to the invention are preferably supported on substrates, and there is no limitation as to the substrates, thus those conventionally used in EL elements may be used, such as those consisting of glass, transparent plastics, electric conductive polymer materials or quartz etc.

Respective layers used in the invention may be formed by filing for example by means of known vacuum evaporation method or coating method etc. The layers in which the said silacyclopentadiene derivatives being used are useful industrially, since stability in film state is high without any particular binder such as resins and thus filming and forming may be carried out by means of vacuum evaporation method etc.

There is no particular limitation as to the thickness of thin film in the respective layer thus formed, and so the thickness may be selected properly according to conditions, but generally selected within a range of from 2 nm to 5000 nm.

As the anodes in EL elements according to the invention, those containing metals, alloys, electric conductive compounds and their mixtures with high (more than 4 eV) work function as materials for electrode are preferably used. As examples of such materials for electrode, there may be mentioned metals such as Au, as well as dielectric transparent materials such as CuI, ITO, $SnO_2$ and ZnO etc. The said anodes may be prepared by filming these materials for electrode by means of vacuum evaporation or spattering etc.

In the case to emit from the electrodes, it is desirable that permeability being increased to more than 10% and that resistance of sheet as electrode being preferably below several hundred Ω/square.

Furthermore, the thickness of film is selected generally within a range of from 10 nm to 1 μm, preferably from 10 to 200 nm, due to the material.

On the other hand, as cathodes, those containing metals, alloys, electric conductive compounds and their mixtures with low (less than 4.3 eV) work function as materials for electrode are preferably used. As examples of such materials for electrode, there may be mentioned calcium, magnesium, lithium, aluminium, magnesium alloys, lithium alloys, aluminium alloys, aluminium/lithium mixtures, magnesium/silver mixtures and indium etc. The said cathodes may be prepared by filming these materials for electrode by means of vacuum evaporation or spattering etc. It is desirable that resistance of sheet as electrode being preferably below several hundred Ω/square, and the thickness of film is generally selected within a range of from 10 nm to 1 μm, preferably from 50 to 200 nm.

Although constructions of EL elements according to the invention may take various embodiments as described above, the luminous efficiency is improved by setting a hole-transporting layer.

Hole-transporting materials used in hole-transporting layers are those which can transmit the holes into the luminescent layers properly in the case of the layer being arranged between two electric field applied electrodes and holes being injected from anodes, for example, those having hole-shifting degrees of at least $10^{-6} cm^2/V.sec$ when electric field of from $10^4$ to $10^6$ V/cm being applied. As to such hole-transporting materials, there is no limitation, provided that they have the above-mentioned preferable properties, and they may be selected for use from the group consisting of those conventionally used as hole transporting materials in photoconductive material and those used in hole-transporting layers of EL elements.

As the said hole-transporting materials, there may be mentioned, for example, carbazole derivatives (such as N-phenyl carbazole and polyvinyl carbazole, etc.), triarylamine derivatives (such as N,N'-diphenyl-N,N'-di(3-methylphenyl)4,4'-diaminobiphenyl (TPD), polymers containing aromatic tertiary amines in main chains or branched and 1,1-bis(4-di-p-tolylaminophenyl)cyclohexane, N,N'-diphenyl-N,N'-dinaphtyl-4,4'-diaminobiphenyl etc.), phthalocyanine derivatives (such as non-metals and copper phthalocyanine etc.) as well as polysilanes.

In the layers for transporting electrons in EL elements according to the invention, if multiple electron-transporting materials are used, not only the said silacyclopentadiene derivatives but also another electron-transporting materials may be used. As preferable examples of the said electron-transporting materials, there may be mentioned phenylquinone derivatives (described in Denshi Shashin Gakkai-shi, 30, 3 (1991) etc.) such as

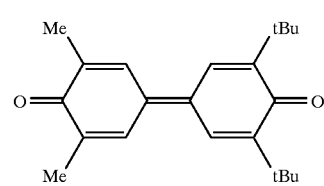

(XXI)

or compounds (described in J. Apply. Phys., 27, 269 (1988) etc.) such as

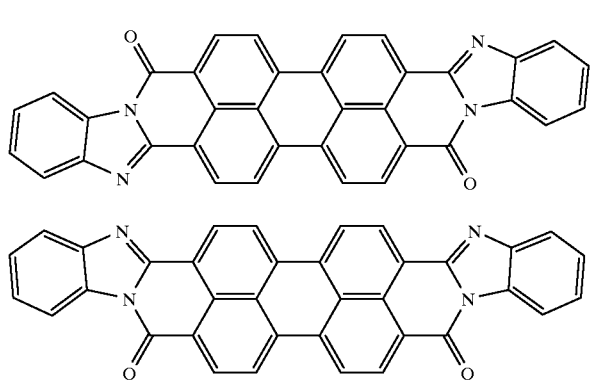

(XXII)

oxadiazole derivatives (described in the above-mentioned literature, Jpn. J. Appl. Phys., 27, L713 (1988), Appl. Phys. Lett., 55, 1489 (1989) etc.), thiophene derivatives (as described in Toku-Kai-Hei 4-212286 official gazette), triazole derivatives (described in Jpn. J. Appl. Phys., 32, L917 (1993), thiadiazole derivatives (described in the 43rd Kobunshi Gakkai Yokoshu, III Pla007 etc.), metal complexes of oxine derivatives (described in Denshi Joho Tushin Gakkai Gijutsu Kenkyu Hokoku, 92 (311), 43(1992) etc.), polymers of quinoxaline derivatives (Jpn.J.Appl.Phys., 33, L250 (1994) etc.), and phenanthroline derivatives (described in the 43rd Kobunshi Toronkai Yokoshu, 14J07).

As luminescent materials used in the invention, there may be used known luminescent materials such as daylight fluorescent materials described in High Molecular Functive Materials Series, "Photofunctive Materials" edited by Kobunshi Gakkai, Kyoritsu Shuppan (1991), P236, fluorescent whitening agents, laser dyes, organic scintillators and various fluorescent analytical agents, wherein the followings are preferable: polycyclic condensated compounds such as anthracene, phenanthrene, pyrene, chrysene, perylene, coronene, ruburene and quinacridone etc.; oligophenylene type compounds such as quarterphenyl; liquid scintillators for scintillation such as 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-tertiary-butyl-2-benzoxazolyl)thiophene, 1,4-diphenyl-1,3-butadiene, 1,6-diphenyl-1,3,5-hexatriene and 1,1,4,4-tetraphenyl-1,3-butadiene etc.; metallic complexes of oxine derivatives described in Toku-Kai-Sho 63-264692 official gazette; coumarine dyes, dicyanomethylene pyran dyes, polymethine dyes, oxobenzanthracene dyes, xanthene dyes, carbostyryl and perylene dyes; oxazine type comounds described in German Patent 2534713 official gazette; stilbene derivatives described in the 40th Oyo Butsurigaku Kankei Rengo Koenkai Koen Yokoshu, 1146 (1993) as well as oxadiazole type compounds described in Toku-Kai-Hei 4-363891 official gazette. Also, silacyclopentadiene derivatives described in the invention may be used.

An example of preferable methods for preparing EL elements according to the invention is illustrated as to the following constitution of elements. To illustrate the preparation method for EL element consisting of anode/the said silacyclopentadiene derivative layer/cathode, at first a desired material for an electrode such as a material for a cathode is formed on an appropriate substrate such as glass plate at the film thickness of less than 1 $\mu$m, preferably within a range of from 10 to 200 nm by means of vacuum evaporation or spattering to prepare an anode, on which a thin film of silacyclopentadiene derivative is then coated.

Although dip coating method, spin coating method, casting method and vacuum evaporation method may be for example mentioned as methods for filming, the vacuum evaporation method is preferable since even film can be easily obtained, impurities are difficult to be mixed into, and pinholes are difficult to be formed.

Then, after formation of the said silacyclopentadiene derivative layer, a thin film consisting of a material for a cathode is coated at the thickness of less than 1 $\mu$m for example by means of vacuum evaporation or spattering etc., to prepare cathode, by which the desired EL element is obtained. In the preparation of the EL element, it is possible to make subsequently a cathode, the said silacyclopentadiene derivative layer and anode by reversing the above-mentioned preparation order.

In the case that direct voltage is applied on the thus obtained EL element, luminescence can be observed from a transparent or semitransparent electrode side when voltage being applied. Furthermore, luminescence is also occurred by applying alternating voltage. Wave form of alternating current applied may be optional.

EXAMPLES

The invention is explained absolutely by means of the following examples, but the invention is not limited to these examples.

Example 1

Synthesis of 1,1-dimethyl-2,3,4,5-tetraphenylsilacyclopentadiene

To 50 ml of tetrahydrofuran (TBF) solution containing 6 ml of ethynylbenzene, 33 ml of 1.6N normal-butyl lithium was added dropwise under a nitrogen gas flow at 0° C. After stirring for 1 hour, 33.3 ml of THF solution containing 3ml of dimethylsilyl chloride was added. After stirring at the room temperature for one night, the deposited solid was filtered and thereafter the obtained reaction solution was concentrated. Water was added to the solution, and then the solution was extracted with diethyl ether. Furthermore, the said diethyl ether layer was washed with water, thereafter dried with magnesium sulfate and concentrated. Then it was recrystallized from hexane, to obtain 5.02 g of bisphenylethynyldimethylsilane.

Then, after substituting inside of a 50 ml two-necked flask containing 2.56 g of naphthalene with argon gas, 140 mg of lithium and 15 ml of THF were added. After stirring for 4 hours, 1.3 g of silane derivative obtained beforehand was added dropwise. It was cooled to 0° C. after 10 minutes, 2.75 g of tertiary-butyl diphenyl silyl chloride was added and stirred for 20 minutes, and then 5.05 g of tetrarnethylethylenediarnine complex of zinc chloride was added. The reaction temperature was returned to the room temperature, and 1.87 g of bromobenzene and 175 mg of bistriphenylphosphine dichloropalladium were added and refluxed for 16 hours. After filtering the deposited solid, the reaction solution was concentrated. Water was added to the concentrated solution obtained, and then the solution was extracted with diethyl ether. Furthermore, the said diethyl ether layer was washed with water, thereafter dried with sodium sulfate and concentrated. After purifring by means of a column chromatography, recrystallization from a mixed solvent of hexane and ethyl acetate was carried out, to obtain 0.97 g of 1,1-dimethyl-2,3,4,5-tetraphenyl silacyclopentadiene in form of light yellow plate crystals.

Examples 2~61

Syntheses of various derivatives

The following various derivatives can be synthesized by the similar methods to the method in Example 1 except that bromobenzene used in Example 1 was substituted with corresponding halogenoaryls and that bisphenylethynyldimethylsilane was substituted with corresponding silanes:

1,1-dimethyl-2,3,4,5-tetrakis(2-methylphenyl) silacyclopentadiene, 1,1-dimethyl-2,3,4,5-tetrakis(3-methylphenyl) silacyclopentadiene, 1,1-dimethyl-2,3,4,5-tetrakis(4-methylphenyl) silacyclopentadiene, 1,1-dimethyl-2,3,4,5-tetrakis(2-ethylphenyl) silacyclopentadiene, 1,1-dimethyl-2,3,4,5-tetrakis(3-ethylphenyl) silacyclopentadiene, 1,1-dimethyl-2,3,4,5-tetrakis(4-ethylphenyl) silacyclopentadiene, 1,1-dimethyl-2,3,4,5-tetrakis(2-tertiary-butylphenyl)silacyclopentadiene,
1,1-dimethyl-2,3,4,5-tetrakis(3-ethylphenyl)silacyclopentadiene,
1,1-dimethyl-2,3,4,5-tetrakis(4-ethylphenyl)silacyclopentadiene,
1,1-dimethyl-2,3,4,5-tetrakis(2-tertiarybutylphenyl)silacyclopentadiene,
1,1-dimethyl-2,3,4,5-tetrakis(3-tertiarybutylphenyl)silacyclopentadiene,
1,1-dimethyl-2,3,4,5-tetrakis(4-tertiarybutylphenyl)silacyclopentadiene,
1,1-dimethyl-2,5-bis(2-methylphenyl)-3,4-diphenylsilacyclopentadiene,
1,1-dimethyl-2,5-bis(3-methylphenyl)-3,4-diphenylsilacyclopentadiene,
1,1-dimethyl-2,5-bis(4-methylphenyl)-3,4-diphenylsilacyclopentadiene,
1,1-dimethyl-2,5-di(2-biphenyl)-3,4-diphenylsilacyclopentadiene,
1,1-dimethyl-2,5-di(3-biphenyl)-3,4-diphenylsilacyclopentadiene,
1,1-dimethyl-2,5-di(4-biphenyl)-3,4-diphenylsilacyclopentadiene,
1,1-dimethyl-2,5-bis(2-trifluoromethylphenyl)-3,4-diphenylsilacyclopentadiene,
1,1-dimethyl-2,5-bis(3-trifluoromethylphenyl)-3,4-diphenylsilacyclopentadiene,
1,1-dimethyl-2,5-bis(4-trifluoromethylphenyl)-3,4-diphenylsilacyclopentadiene,
1,1-dimethyl-2,5-bis(2-fluorophenyl)-3,4-diphenylsilacyclopentadiene,
1,1-dimethyl-2,5-bis(3-fluorophenyl)-3,4-diphenylsilacyclopentadiene,
1,1-dimethyl-2,5-bis(4-fluorophenyl)-3,4-diphenylsilacyclopentadiene,
1,1-dimethyl-2,5-bis(2-methoxyphenyl)-3,4-diphenylsilacyclopentadiene,
1,1-dimethyl-2,5-bis(3-methoxyphenyl)-3,4-diphenylsilacyclopentadiene,
1,1-dimethyl-2,5-bis(4-methoxyphenyl)-3,4-diphenylsilacyclopentadiene,
1,1-dimethyl-2,5-bis(2-cyanophenyl)-3,4-diphenylsilacyclopentadiene,
1,1-dimethyl-2,5-bis(3-cyanophenyl)-3,4-diphenylsilacyclopentadiene,
1,1-dimethyl-2,5-bis(4-cyanophenyl)-3,4-diphenylsilacyclopentadiene,
1,1-dimethyl-2,5-bis{2-(2-benzoxazolyl)phenyl}-3,4-diphenylsilacyclopentadiene,
1,1-dimethyl-2,5-bis{3-(2-benzoxazolyl)phenyl}-3,4-diphenylsilacyclopentadiene,
1,1-dimethyl-2,5-bis{4-(2-benzoxazolyl)phenyl}-3,4-diphenylsilacyclopentadiene,
1,1-dimethyl-2,5-bis{2-(2-benzothiazolyl)phenyl}-3,4-diphenylsilacyclopentadiene,
1,1-dimethyl-2,5-bis{3-(2-benzothiazolyl)phenyl}-3,4-diphenylsilacyclopentadiene,
1,1-dimethyl-2,5-bis{4-(2-benzothiazolyl)phenyl}-3,4-diphenylsilacyclopentadiene,
1,1-dimethyl-2,5-bis{2-(5-methyl-2-benzoxazolyl)phenyl}-3,4-diphenylsilacyclopentadiene,
1,1-dimethyl-2,5-bis{3-(5-methyl-2-benzoxazolyl)phenyl}-3,4-diphenylsilacyclopentadiene,
1,1-dimethyl-2,5-bis{4-(5-methyl-2-benzoxazolyl)phenyl}-3,4-diphenylsilacyclopentadiene,
1,1-dimethyl-2,5-di(1-naphthyl)-3,4-diphenylsilacyclopentadiene,
1,1-dimethyl-2,5-di(2-methyl-1-naphthyl)-3,4-diphenylsilacyclopentadiene,
1,1-dimethyl-2,5-di(2-methoxy-1-naphthyl)-3,4-diphenylsilacyclopentadiene,
1,1-dimethyl-2,5-di(2-naphthyl)-3,4-diphenylsilacyclopentadiene,
1,1-dimethyl-2,5-di(6-methoxy-2-naphthyl)-3,4-diphenylsilacyclopentadiene,
1,1-dimethyl-2,5-di(7-methoxy-2-naphthyl)-3,4-diphenylsilacyclopentadiene,
1,1-dimethyl-2,5-di(2-benzothienyl)-3,4-diphenylsilacyclopentadiene,
1,1-dimethyl-2,5-di(3-benzothienyl)-3,4-diphenylsilacyclopentadiene,
1,1-dimethyl-2,5-bis(3-methyl-2-benzothienyl)-3,4-diphenylsflacyclopentadiene,
1,1-dimethyl-2,5-bis(3-phenyl-2-benzothienyl)-3,4-diphenylsilacyclopentadiene,
1,1-dimethyl-2,5-bis(2-methyl-3-benzothienyl)-3,4-diphenylsilacyclopentadiene,
1,1-dimethyl-2,5-bis(2-phenyl-3-benzothienyl)-3,4diphenylsilacyclopentadiene,
1,1-dimethyl-2,5-di(2-benzothiazolyl)-3,4-diphenylsilacyclopentadiene,
1,1-dimethyl-2,5-di(2-benzoxazolyl)-3,4-diphenylsilacyclopentadiene,
1,1-dimethyl-2,5-bis(5-methyl-2-benzoxazolyl)-3,4-diphenylsilacyclopentadiene,
1,1-dimethyl-2,5-bis(5-phenyl-2-benzoxazolyl)-3,4-diphenylsilacyclopentadiene,
1,1-dimethyl-2,5-bis(5-methyl-2-benzothiazolyl)-3,4-diphenylsilacyclopentadiene,
1,1-dimethyl-2,5-bis(5-phenyl-2-benzothiazolyl)-3,4-diphenylsilacyclopentadiene,
1,1-dimethyl-2,5-di(2-benzofuranyl)-3,4-diphenylsilacyclopentadiene,
1,1-dimethyl-2,5-di(3-benzofuranyl)-3,4-diphenylsilacyclopentadiene,
1,1-dimethyl-2,5-di(2-benzothienyl)-3,4-diphenylsilacyclopentadiene,
1,1-dimethyl-2,5-bis(3,4-difluorophenyl-3,4-diphenylsilacyclopentadiene,
1,1-dimethyl-2,5-bis(3,4,5-trifluorophenyl)-3,4-diphenylsilacyclopentadiene or
1,1-dimethyl-2,5-bis(2,3,4,5,6-pentafluorophenyl)-3,4-diphenylsflacyclopentadiene.

Example 62
Synthesis of 1,1-diethyl-2,3,4,5-tetraphenylsilacyclopentadiene
1,1-diethyl-2,3,4,5-tetraphenylsilacyclopentadiene can be synthesized by the method in accordance with Example 1 except that bisphenylethynyldimethylsilane used in Example 1 was substituted with bisphenylethynyldiethylsilane.

Example 63~122
Synthesis of various derivatives
The following various derivatives can be synthesized by the similar methods to the method in Example 62 except that bromobenzene used in Example 62 was substituted with corresponding halogenoaryls and that bisphenylethynyldiethyl-silane was substituted with corresponding silanes:
1,1-diethyl-2,3,4,5-tetrakis(2-methylphenyl)silacyclopentadiene,
1,1-diethyl-2,3,4,5-tetrakis(3-methylphenyl)silacyclopentadiene, 1,1-diethyl-2,3,4,5-tetrakis(4-methylphenyl)
    silacyclopentadiene,
1,1-diethyl-2,3,4,5-tetrakis(2-ethylphenyl)
    silacyclopentadiene,
1,1-diethyl-2,3,4,5-tetrakis(3-ethylphenyl)
    silacyclopentadiene,
1,1-diethyl-2,3,4,5-tetrakis(4-ethylphenyl)
    silacyclopentadiene,
1,1-diethyl-2,3,4,5-tetrakis(2-tertiarybutylphenyl)
    silacyclopentadiene,
1,1-diethyl-2,3,4,5-tetrakis(3-tertiarybutylphenyl)
    silacyclopentadiene,
1,1-diethyl-2,3,4,5-tetrakis(4-tertiarybutylphenyl)
    silacyclopentadiene,
1,1-diethyl-2,5-bis(2-methylphenyl)-3,4-
    diphenylsilacyclopentadiene,
1,1-diethyl-2,5-bis(3-methylphenyl)-3,4-
    diphenylsflacyclopentadiene,
1,1-diethyl-2,5-bis(4-methylphenyl)-3,4-
    diphenylsilacyclopentadiene,
1,1-diethyl-2,5-di(2-biphenyl)-3,4-
    diphenylsilacyclopentadiene,
1,1-diethyl-2,5-di(3-biphenyl)-3,4-
    diphenylsilacyclopentadiene,
1,1-diethyl-2,5-di(4-biphenyl)-3,4-
    diphenylsilacyclopentadiene,
1,1-diethyl-2,5-bis(2-trifluoromethylphenyl)-3,4-
    diphenylsilacyclopentadiene,
1,1-diethyl-2,5-bis(3-trifluoromethylphenyl)-3,4-
    diphenylsilacyclopentadiene,
1,1-diethyl-2,5-bis(4-trifluoromethylphenyl)-3,4-
    diphenylsilacyclopentadiene,
1,1-diethyl-2,5-bis(2-fluorophenyl)-3,
    4diphenylsilacyclopentadiene,
1,1-diethyl-2,5-bis(3-fluorophenyl)-3,4-
    diphenylsilacyclopentadiene,
1,1-diethyl-2,5-bis(4-fluorophenyl)-3,4-
    diphenylsilacyclopentadiene,
1,1-diethyl-2,5-bis(2-methoxyphenyl)-3,4-
    diphenylsilacyclopentadiene,
1,1-diethyl-2,5-bis(3 -methoxyphenyl)-3,4-
    diphenylsilacyclopentadiene,
1,1-diethyl-2,5-bis(4-methoxyphenyl)-3,4-
    diphenylsilacyclopentadiene,
1,1-diethyl-2,5-bis(2-cyanophenyl)-3,4-
    diphenylsilacyclopentadiene,
1,1-diethyl-2,5-bis(3-cyanophenyl)-3,4-
    diphenylsilacyclopentadiene,
1,1-diethyl-2,5-bis(4-cyanophenyl)-3,4-
    diphenylsilacyclopentadiene,
1,1-diethyl-2,5-bis{2-(2-benzoxazolyl)phenyl}-3,4-
    diphenylsilacyclopentadiene,
1,1-diethyl-2,5-bis{3-(2-benzoxazolyl)phenyl}-3,4-
    diphenylsilacyclopentadiene,
1,1-diethyl-2,5-bis{4-(2-benzoxazolyl)phenyl}-3,4-
    diphenylsilacyclopentadiene,
1,1-diethyl-2,5-bis{2-(2-benzothiazolyl)phenyl}-3,4-
    diphenylsilacyclopentadiene,
1,1-diethyl-2,5-bis{3-(2-benzothiazolyl)phenyl}-3,4-
    diphenylsilacyclopentadiene,
1,1-diethyl-2,5-bis{4-(2-benzothiazolyl)phenyl}-3,4-
    diphenylsilacyclopentadiene,
1,1-diethyl-2,5-bis{2-(5-methyl2-benzoxazolyl)phenyl}-3,
    4-diphenylsilacyclopentadiene,
1,1-diethyl-2,5-bis{3-(5-methyl-2-benzoxazolyl)phenyl}-3,
    4-diphenylsilacyclopentadiene,
1,1-diethyl-2,5-bis{4-(5-methyl-2-benzoxazolyl)phenyl}-3,
    4-diphenylsilacyclopentadiene,
1,1-diethyl-2,5-di(1-naphthyl)-3,4-
    diphenylsilacyclopentadiene,
1,1-diethyl-2,5-di(2-methyl-1-naphthyl)-3,4-
    diphenylsilacyclopentadiene,
1,1-diethyl-2,5-di(2-methoxy-1-naphthyl)-3,4-
    diphenylsilacyclopentadiene,
1,1-diethyl-2,5-di(2-naphthyl)-3,4-
    diphenylsilacyclopentadiene,
1,1-diethyl-2,5-di(6-methoxy-2-naphthyl)-3,4-
    diphenylsilacyclopentadiene,
1,1-diethyl-2,5-di(7-methoxy-2-naphthyl)-3,4-
    diphenylsilacyclopentadiene,
1,1-diethyl-2,5-di(2-benzothienyl)-3,4-
    diphenylsilacyclopentadiene,
1,1-diethyl-2,5-di(3-benzothienyl)-3,4-
    diphenylsilacyclopentadiene,
1,1-diethyl-2,5-bis(3-methyl-2-benzothienyl)-3,4-
    diphenylsilacyclopentadiene,
1,1-diethyl-2,5-bis(3-phenyl-2-benzothienyl)-3,4-
    diphenylsilacyclopentadiene,
1,1-diethyl-2,5-bis(2-methyl-3-benzothienyl)-3,4-
    diphenylsilacyclopentadiene,
1,1-diethyl-2,5-bis(2-phenyl-3-benzothienyl)-3,4-
    diphenylsilacyclopentadiene,
1,1-diethyl-2,5-di(2-benzothiazolyl)-3,4-
    diphenylsilacyclopentadiene,
1,1-diethyl-2,5-di(2-benzoxazolyl)-3,4-
    diphenylsilacyclopentadiene,
1,1-diethyl-2,5-bis(5-methyl-2-benzoxazolyl)-3,4-
    diphenylsilacyclopentadiene,
1,1-diethyl-2,5-bis(5-phenyl-2-benzoxazolyl)-3,4-
    diphenylsilacyclopentadiene,
1,1-diethyl-2,5-bis(5-methyl-2-benzothiazolyl)-3,4-
    diphenylsilacyclopentadiene,
1,1-diethyl-2,5-bis(5-phenyl-2-benzothiazolyl)-3,4-
    diphenylsilacyclopentadiene,
1,1-diethyl-2,5-di(2-benzofuranyl)-3,4-
    diphenylsilacyclopentadiene,
1,1-diethyl-2,5-di(3-benzofuranyl)-3,4-
    diphenylsilacyclopentadiene,
1,1-diethyl-2,5-di(2-benzothienyl)-3,4-
    diphenylsilacyclopentadiene,
1,1-diethyl-2,5-bis(3,4-difluorophenyl)-3,
    4diphenylsilacyclopentadiene,
1,1-diethyl-2,5-bis(3,4,5-trifluorophenyl)-3,4-
    diphenylsilacyclopentadiene or
1,1-diethyl-2,5-bis(2,3,4,5,6-pentafluorophenyl)-3,4-
    diphenylsilacyclopentadiene.

Example 123
Synthesis of 1-ethyl-1-methyl-2,3,4,5-tetraphenylsilacyclopentadiene 1-ethyl-1-methyl-2,3,4,5-tetraphenylsilacyclopentadiene can be synthesized by the method in accordance with Example 1 except that bisphenylethynylethylmethyl-silane used in Example 1 was substituted with bisphenylethnylethylmethylsilane.

Example 124~183
Synthesis of various derivatives

The following various derivatives can be synthesized by the similar methods to the method in Example 123 except that bromobenzene used in Example 123 was substituted with corresponding halogenoaryls and that bisphenylethynylethyl-methylsilane was substituted with corresponding silanes:

1-ethyl-1-methyl-2,3,4,5-tetrakis(2-methylphenyl)
    silacyclopentadiene, 1-ethyl-1-methyl-2,3,4,5-tetrakis(3-methylphenyl) silacyclopentadiene,
1-ethyl-1-methyl-2,3,4,5-tetrakis(4-methylphenyl) silacyclopentadiene,
1-ethyl-1-methyl-2,3,4,5-tetrakis(2-ethylphenyl) silacyclopentadiene,
1-ethyl-1-methyl-2,3,4,5-tetrakis(3-ethylphenyl) silacyclopentadiene,
1-ethyl-1-methyl-2,3,4,5-tetrakis(4-ethylphenyl) silacyclopentadiene,
1-ethyl-1-methyl-2,3,4,5-tetrakis(2-tertiarybutylphenyl) silacyclopentadiene,
1-ethyl-1-methyl-2,3,4,5-tetrakis(3-tertiarybutylphenyl) silacyclopentadiene,
1-ethyl-1-methyl-2,3,4,5-tetrakis(4-tertiarybutylphenyl) silacyclopentadiene,
1-ethyl-1-methyl-2,5-bis(2-methylphenyl)-3,4-diphenylsilacyclopentadiene,
1-ethyl-1-methyl-2,5-bis(3-methylphenyl)-3,4-diphenylsilacyclopentadiene,
1-ethyl-1-methyl-2,5-bis(4-methylphenyl)-3,4-diphenylsilacyclopentadiene,
1-ethyl-1-methyl-2,5-di(2-biphenyl)-3,4-4phenylsilacyclopentadiene,
1-ethyl-1-methyl-2,5-di(3-biphenyl)-3,4-diphenylsilacyclopentadiene,
1-ethyl-1-methyl-2,5-di(4-biphenyl)-3,4-diphenylsilacyclopentadiene,
1-ethyl-1-methyl-2,5-bis(2-trifluoromethylphenyl)-3,4-diphenylsilacyclopentadiene,
1-ethyl-1-methyl-2,5-bis(3-trifluoromethylphenyl)-3,4-diphenylsilacyclopentadiene,
1-ethyl-1-methyl-2,5-bis(4-trifluoromethylphenyl)-3,4-diphenylsflacyclopentadiene,
1-ethyl-1-methyl-2,5-bis(2-fluorophenyl)-3,4-diphenylsilacyclopentadiene,
1-ethyl-1-methyl-2,5-bis(3-fluorophenyl)-3,4-diphenylsilacyclopentadiene,
1-ethyl-1-methyl-2,5-bis(4-fluorophenyl)-3,4-diphenylsilacyclopentadiene,
1-ethyl-1-methyl-2,5-bis(2-methoxyphenyl)-3,4-diphenylsilacyclopentadiene,
1-ethyl-1-methyl-2,5-bis(3-methoxyphenyl)-3,4-diphenylsilacyclopentadiene,
1-ethyl-1-methyl-2,5-bis(4-methoxyphenyl)-3,4-diphenylsilacyclopentadiene,
1-ethyl-1-methyl-2,5-bis(2-cyanophenyl)-3,4-diphenylsilacyclopentadiene,
1-ethyl-1-methyl-2,5-bis(3-cyanophenyl)-3,4-diphenylsilacyclopentadiene,
1-ethyl-1-methyl-2,5-bis(4-cyanophenyl)-3,4-diphenylsilacyclopentadiene,
1-ethyl-1-methyl-2,5-bis{2-(2-benzoxazolyl)phenyl}-3,4-diphenylsilacyclopentadiene,
1-ethyl-1-methyl-2,5-bis{3-(2-benzoxazolyl)phenyl}-3,4-diphenylsilacyclopentadiene,
1-ethyl-1-methyl-2,5-bis{4-(2-benzoxazolyl)phenyl}-3,4-diphenylsilacyclopentadiene,
1-ethyl-1-methyl-2,5-bis{2-(2-benzothiazolyl)phenyl}-3,4-diphenylsilacyclopentadiene,
1-ethyl-1-methyl-2,5-bis{3-(2-benzothiazolyl)phenyl}-3,4-diphenylsilacyclopentadiene,
1-ethyl-1-methyl-2,5-bis{4-(2-benzothiazolyl)phenyl}-3,4-diphenylsilacyclopentadiene,
1-ethyl-1-methyl-2,5-bis{2-(5-methyl-2-benzoxazolyl) phenyl}-3,4-diphenylsilacyclopentadiene,
1-ethyl-1-methyl-2,5-bis{3-(5-methyl-2-benzoxazolyl) phenyl}-3,4-diphenylsilacyclopentadiene,
1-ethyl-1-methyl-2,5-bis{4(5-methyl-2-benzoxazolyl) phenyl}-3,4-diphenylsilacyclopentadiene,
1-ethyl-1-methyl-2,5-di(1-naphthyl)-3,4-diphenylsilacyclopentadiene,
1-ethyl-1-methyl-2,5-di(2-methyl-1-naphthyl)-3,4-diphenylsilacyclopentadiene,
1-ethyl-1-methyl-2,5-di(2-methoxy-1-naphthyl)-3,4-diphenylsilacyclopentadiene,
1-ethyl-1-methyl-2,5-di(2-naphthyl)-3,4-diphenylsilacyclopentadiene,
1-ethyl-1-methyl-2,5-di(6-methoxy-2-naphthyl)-3,4-diphenylsilacyclopentadiene,
1-ethyl-1-methyl-2,5-di(7-methoxy-2-naphthyl)-3,4-diphenylsilacyclopentadiene,
1-ethyl-1-methyl-2,5-di(2-benzothienyl)-3,4-diphenylsilacyclopentadiene,
1-ethyl-1-methyl-2,5-di(3-benzothienyl)-3,4-diphenylsilacyclopentadiene,
1-ethyl-1-methyl-2,5-bis(3-methyl-2-benzothienyl)-3,4-diphenylsilacyclopentadiene,
1-ethyl-1-methyl-2,5-bis(3-phenyl-2-benzothienyl)-3,4-diphenylsilacyclopentadiene,
1-ethyl-1-methyl-2,5-bis(2-methyl-3-benzothienyl)-3,4-diphenylsilacyclopentadiene,
1-ethyl-1-methyl-2,5-bis(2-phenyl-3-benzothienyl)-3,4-diphenylsilacyclopentadiene,
1-ethyl-1-methyl-2,5-bis(2-benzothiazolyl)-3,4-diphenylsilacyclopentadiene,
1-ethyl-1-methyl-2,5-di(2-benzoxazolyl)-3,4diphenylsilacyclopentadiene,
1-ethyl-1-methyl-2,5-bis(5-methyl-2-benzoxazolyl)-3,4-diphenylsilacyclopentadiene,
1-ethyl-1-methyl-2,5-bis(5-phenyl-2-benzoxazolyl)-3,4diphenylsilacyclopentadiene,
1-ethyl-1-methyl-2,5-bis(5-methyl-2-benzothiazolyl)-3,4-diphenylsilacyclopentadiene,
1-ethyl-1-methyl-2,5-bis(5-phenyl-2-benzothiazolyl)-3,4-diphenylsilacyclopentadiene,
1-ethyl-1-methyl-2,5-di(2-benzofuranyl)-3,4-diphenylsilacyclopentadiene,
1-ethyl-1-methyl-2,5-di(3-benzofuranyl)-3,4-diphenylsilacyclopentadiene,
1-ethyl-1-methyl-2,5-di(2-benzothienyl)-3,4-diphenylsilacyclopentadiene,
1-ethyl-1-methyl-2,5-bis(3,4-difluorophenyl)-3,4-diphenylsilacyclopentadiene,
1-ethyl-1-methyl-2,5-bis(3,4,5-trifluorophenyl)-3,4-diphenylsilacyclopentadiene or
1-ethyl-1-methyl-2,5-bis(2,3,4,5,6-pentafluorophenyl)-3,4-diphenylsflacyclopentadiene.

Example 184
Synthesis of 1,1-diphenyl-2,3,4,5-tetraphenylsilacyclopentadiene 1,1-diphenyl-2,3,4,5-tetraphenylsilacyclopentadiene can be synthesized by the method in accordance with Example 1 except that bisphenylethynyldimethylsilane used in Example 1 was substituted with bisphenylethynyldiphenyl-silane.

Example 185~244
Synthesis of various derivatives

The following various derivatives can be sythesized by the similar methods to the method in Example 184 except that bromobenzene used in Example 184 was substituted with corresponding halogenoaryls and that bisphenylethynyldiphenyl-silane was substituted with corresponding silanes:

1,1-diphenyl-2,3,4,5-tetrakis(2-methylphenyl)silacyclopentadiene,
1,1-diphenyl-2,3,4,5-tetrakis(3-methylphenyl)silacyclopentadiene,
1,1-diphenyl-2,3,4,5-tetrakis(4-methylphenyl)silacyclopentadiene,
1,1-diphenyl-2,3,4,5-tetrakis(2-ethylphenyl)silacyclopentadiene,
1,1-diphenyl-2,3,4,5-tetrakis(3-ethylphenyl)silacyclopentadiene,
1,1-diphenyl-2,3,4,5-tetrakis(4-ethylphenyl)silacyclopentadiene,
1,1-diphenyl-2,3,4,5-tetrakis(2-tertiarybutylphenyl)silacyclopentadiene,
1,1-diphenyl-2,3,4,5-tetrakis(3-tertiarybutylphenyl)silacyclopentadiene,
1,1-diphenyl-2,3,4,5-tetrakis(4-tertiarybutylphenyl)silacyclopentadiene,
1,1-diphenyl-2,5-bis(2-methylphenyl)-3,4-diphenylsilacyclopentadiene,
1,1-diphenyl-2,5-bis(3-methylphenyl)-3,4-diphenylsilacyclopentadiene,
1,1-diphenyl-2,5-bis(4-methylphenyl)-3,4-diphenylsilacyclopentadiene,
1,1-diphenyl-2,5-di(2-biphenyl)-3,4-diphenylsilacyclopentadiene,
1,1-diphenyl-2,5-di(3-biphenyl)-3,4-diphenylsilacyclopentadiene,
1,1-diphenyl-2,5-di(4-biphenyl)-3,4-diphenylsilacyclopentadiene,
1,1-diphenyl-2,5-bis(2-trifluoromethylphenyl)-3,4-diphenylsflacyclopentadiene,
1,1-diphenyl-2,5-bis(3-trifluoromethylphenyl)-3,4-diphenylsilacyclopentadiene,
1,1-diphenyl-2,5-bis(4-trifluoromethylphenyl)-3,4-diphenylsilacyclopentadiene,
1,1-diphenyl-2,5-bis(2-fluorophenyl)-3,4-diphenylsilacyclopentadiene,
1,1-diphenyl-2,5-bis(3-fluorophenyl)-3,4-diphenylsilacyclopentadiene,
1,1-diphenyl-2,5-bis(4-fluorophenyl)-3,4-diphenylsilacyclopentadiene,
1,1-diphenyl-2,5-bis(2-methoxyphenyl)-3,4-diphenylsilacyclopentadiene,
1,1-diphenyl-2,5-bis(3-methoxyphenyl)-3,4-diphenylsilacyclopentadiene,
1,1-diphenyl-2,5-bis(4-methoxyphenyl)-3,4-diphenylsilacyclopentadiene,
1,1-diphenyl-2,5-bis(2-cyanophenyl)-3,4-diphenylsilacyclopentadiene,
1,1-diphenyl-2,5-bis(3-cyanophenyl)-3,4-diphenylsilacyclopentadiene,
1,1-diphenyl-2,5-bis(4-cyanophenyl)-3,4-diphenylsilacyclopentadiene,
1,1-diphenyl-2,5-bis{2-(2-benzoxazolyl)phenyl}-3,4-diphenylsilacyclopentadiene,
1,1-diphenyl-2,5-bis{3-(2-benzoxazolyl)phenyl}-3,4-diphenylsilacyclopentadiene,
1,1-diphenyl-2,5-bis{4-(2-benzoxazolyl)phenyl}-3,4-diphenylsilacyclopentadiene,
1,1-diphenyl-2,5-bis{2-(2-benzothiazolyl)phenyl}-3,4-diphenylsilacyclopentadiene,
1,1-diphenyl-2,5-bis{3-(2-benzothiazolyl)phenyl}-3,4-diphenylsilacyclopentadiene,
1,1-diphenyl-2,5-bis{4-(2-benzothiazolyl)phenyl}-3,4-diphenylsilacyclopentadiene,
1,1-diphenyl-2,5-bis{2-(5-methyl-2-benzoxazolyl)phenyl}-3,4-diphenylsilacyclopentadiene,
1,1-diphenyl-2,5-bis{3-(5-methyl-2-benzoxazolyl)phenyl}-3,4-diphenylsilacyclopentadiene,
1,1-diphenyl-2,5-bis{4-(5-methyl-2-benzoxazolyl)phenyl}-3,4-diphenylsilacyclopentadiene,
1,1-diphenyl-2,5-di(1-naphthyl)-3,4-diphenylsilacyclopentadiene,
1,1-diphenyl-2,5-di(2-methyl-1-naphtyl)-3,4-diphenylsilacyclopentadiene,
1,1-diphenyl-2,5-di(2-methoxy-1-naphtyl)-3,4-diphenylsilacyclopentadiene,
1,1-diphenyl-2,5-di(2-naphthyl)-3,4-diphenylsilacyclopentadiene,
1,1-diphenyl-2,5-di(6-methoxy-2-naphtyl)3,4-diphenylsilacyclopentadiene,
1,1-diphenyl-2,5-di(7-methoxy-2-naphtyl)3,diphenylsilacyclopentadiene,
1,1-diphenyl-2,5-di(2-benzothienyl)-3,4-diphenylsilacyclopentadiene,
1,1-diphenyl-2,5-di(3-benzothienyl)-3,4-diphenylsilacyclopentadiene,
1,1-diphenyl-2,5-bis(3-methyl-2-benzothienyl)-3,4-diphenylsflacyclopentadiene,
1,1-diphenyl-2,5-bis(3-phenyl-2-benzothienyl)-3,4-diphenylsilacyclopentadiene,
1,1-diphenyl-2,5-bis(2-methyl-3-benzothienyl)-3,4-diphenylsilacyclopentadiene,
1,1-diphenyl-2,5-bis(2-phenyl-3-benzothienyl)-3,4-diphenylsflacyclopentadiene,
1,1-diphenyl-2,5-di(2-benzothiazolyl)-3,4-diphenylsilacyclopentadiene,
1,1-diphenyl-2,5-di(2-benzoxazolyl)-3,4-diphenylsilacyclopentadiene,
1,1-diphenyl-2,5-bis(5-methyl-2-benzoxazolyl)-3,4-diphenylsilacyclopentadiene,
1,1-diphenyl-2,5-bis(5-phenyl-2-benzoxazolyt)-3,4-diphenylsilacyclopentadiene,
1,1-diphenyl-2,5-bis(5-methyl-2-benzothiazolyl)-3,4-diphenylsilacyclopentadiene,
1,1-diphenyl-2,5-bis(5-phenyl-2-benzothiazolyl)-3,4-diphenylsilacyclopentadiene,
1,1-diphenyl-2,5-di(2-benzofuranyl)-3,4-diphenylsilacyclopentadiene,
1,1-diphenyl-2,5-di(3-benzofuranyl)-3,4-diphenylsilacyclopentadiene,
1,1-diphenyl-2,5-di(2-benzothienyl)-3,4-diphenylsilacyclopentadiene,
1,1-diphenyl-2,5-bis(3,4-difluorophenyl)-3,4-diphenylsilacyclopentadiene,
1,1-diphenyl-2,5-bis(3,4,5-trifluorophenyl)-3,4-diphenylsflacyclopentadiene and
1,1-diphenyl-2,5-bis(2,3,4,5,6-pentafluorophenyl)-3,4-diphenylsilacyclopentadiene.

Example 245

Synthesis of 1-tertiarybutyl-1-phenyl-2,3,4,5-tetraphenylsilacyclopentadiene 1-tertiarybutyl-1-phenyl-2,3,4,5-tetraphenylsilacyclopentadiene can be synthesized by the method in accordance with Example 1 except that bisphenyl-ethynyldimethylsilane used in Example 1 was substituted with bisphenylethynyltertiarybutyl-1-phenyl-2,3,4,5-tetraphenylsilacyclopentadiene.

Example 246~305

Synthesis of various derivatives

The following various derivatives can be synthesized by the similar methods to the method in Example 245 except that bromobenzene used in Example 245 was substituted with corresponding halogenoaryls and that bisphenylethynyltertiary-butylphenylsilane was substituted with corresponding silanes:

1-tertiarybutyl-1-phenyl-2,3,4,5-tetrakis(2-methylphenyl) silacyclopentadiene,
1-tertiarybutyl-1-phenyl-2,3,4,5-tetrakis(3-methylphenyl) silacyclopentadiene,
1-tertiarybutyl-1-phenyl-2,3,4,5-tetrakis(4-methylphenyl) silacyclopentadiene,
1-tertiarybutyl-1-phenyl-2,3,4,5-tetrakis(2-ethylphenyl) silacyclopentadiene,
1-tertiarybutyl-1-phenyl-2,3,4,5-tetrakis(3-ethylphenyl) silacyclopentadiene,
1-tertiarybutyl-1-phenyl-2,3,4,5-tetrakis(4-ethylphenyl) silacyclopentadiene,
1-tertiarybutyl-1-phenyl-2,3,4,5-tetrakis(2-tertiarybutylphenyl) silacyclopentadiene,
1-tertiarybutyl-1-phenyl-2,3,4,5-tetrakis(3-tertiarybutylphenyl) silacyclopentadiene,
1-tertiarybutyl-1-phenyl-2,3,4,5-tetrakis(4-tertiarybutylphenyl) silacyclopentadiene,
1-tertiarybutyl-1-phenyl-2,5-bis(2-methylphenyl)-3,4-diphenylsilacyclopentadiene,
1-tertiarybutyl-1-phenyl-2,5-bis(3-methylphenyl)-3,4-diphenylsilacyclopentadiene,
1-tertiarybutyl-1-phenyl-2,5-bis(4-methylphenyl)-3,4-diphenylsilacyclopentadiene,
1-tertiarybutyl-1-phenyl-2,5-di(2-biphenyl)-3,4-diphenylsilacyclopentadiene,
1-tertiarybutyl-1-phenyl-2,5-di(3-biphenyl)-3,4-diphenylsilacyclopentadiene,
1-tertiarybutyl-1-phenyl-2,5-di(4-biphenyl)-3,4-diphenylsilacyclopentadiene,
1-tertiarybutyl-1-phenyl-2,5-di(2-trifuoromethylphenyl)-3,4-diphenylsilacyclopentadiene,
1-tertiarybutyl-1-phenyl-2,5-di(3-trifluoromethylphenyl)-3,4-diphenylsilacyclopentadiene,
1-tertiarybutyl-1-phenyl-2,5-di(4-trifluoromethylphenyl)-3,4-diphenylsilacyclopentadiene,
1-tertiarybutyl-1-phenyl-2,5-bis(2-fluorophenyl)-3,4-diphenylsilacyclopentadiene,
1-tertiarybutyl-1-phenyl-2,5-bis(3-fluorophenyl)-3,4-diphenylsilacyclopentadiene,
1-tertiarybutyl-1-phenyl-2,5-bis(4-fluorophenyl)-3,4-diphenylsilacyclopentadiene,
1-tertiarybutyl-1-phenyl-2,5-bis(2-methoxyphenyl)-3,4-diphenylsilacyclopentadiene,
1-tertiarybutyl-1-phenyl-2,5-bis(3-methoxyphenyl)-3,4-diphenylsilacyclopentadiene,
1-tertiarybutyl-1-phenyl-2,5-bis(4-methoxyphenyl)-3,4-diphenylsilacyclopentadiene,
1-tertiarybutyl-1-phenyl-2,5-bis(2-cyanophenyl)-3,4-diphenylsilacyclopentadiene,
1-tertiarybutyl-1-phenyl-2,5-bis(3-cyanophenyl)-3,4-diphenylsilacyclopentadiene,
1-tertiarybutyl-1-phenyl-2,5-bis(4-cyanophenyl)-3,4-diphenylsilacyclopentadiene,
1-tertiarybutyl-1-phenyl-2,5-bis{2-(2-benzoxazolyl)phenyl}-3,4-diphenylsilacyclopentadiene,
1-tertiarybutyl-1-phenyl-2,5-bis{3-(2-benzoxazolyl)phenyl}-3,4-diphenylsilacyclopentadiene,
1-tertiarybutyl-1-phenyl-2,5-bis{4-(2-benzoxazolyl)phenyl}-3,4-diphenylsilacyclopentadiene,
1-tertiarybutyl-1-phenyl-2,5-bis{2-(2-benzothiazolyl)phenyl}-3,4-diphenylsilacyclopentadiene,
1-tertiarybutyl-1-phenyl-2,5-bis{3-(2-benzothiazolyl)phenyl}-3,4-diphenylsilacyclopentadiene,
1-tertiarybutyl-1-phenyl-2,5-bis{4-(2-benzothiazolyl)phenyl}-3,4-diphenylsilacyclopentadiene,
1-tertiarybutyl-1-phenyl-2,5-bis{2-(5-methyl-2-benzoxazolyl)phenyl}-3,4-diphenylsilacyclopentadiene,
1-tertiarybutyl-1-phenyl-2,5-bis{3-(5-methyl-2-benzoxazolyl)phenyl}-3,4-diphenylsilacyclopentadiene,
1-tertiarybutyl-1-phenyl-2,5-bis{4-(5-methyl-2-benzoxazolyl)phenyl}-3,4-diphenylsilacyclopentadiene,
1-tertiarybutyl-1-phenyl-2,5-bis(1-naphthyl)-3,4-diphenylsilacyclopentadiene,
1-tertiarybutyl-1-phenyl-2,5-bis(2-methyl-1-naphthyl)-3,4-diphenylsilacyclopentadiene,
1-tertiarybutyl-1-phenyl-2,5-bis(2-methoxy-1-naphthyl)-3,4-diphenylsilacyclopentadiene,
1-tertiarybutyl-1-phenyl-2,5-di(2-naphthyl)-3,4-diphenylsilacyclopentadiene,
1-tertiarybutyl-1-phenyl-2,5-di(6-methoxy-2-naphthyl)-3,4-diphenylsilacyclopentadiene,
1-tertiarybutyl-1-phenyl-2,5-di(7-methoxy-2-naphthyl)-3,4-diphenylsilacyclopentadiene,
1-tertiarybutyl-1-phenyl-2,5-di(2-benzothienyl)-3,4-diphenylsilacyclopentadiene,
1-tertiarybutyl-1-phenyl-2,5-di(3-benzothienyl)-3,4-diphenylsilacyclopentadiene,
1-tertiarybutyl-1-phenyl-2,5-bis(3-methyl-2-benzothienyl)-3,4-diphenylsilacyclopentadiene,
1-tertiarybutyl-1-phenyl-2,5-bis(3-phenyl-2-benzothienyl)-3,4-diphenylsilacyclopentadiene,
1-tertiarybutyl-1-phenyl-2,5-bis(2-methyl-3-benzothienyl)-3,4-diphenylsflacyclopentadiene,
1-tertiarybutyl-1-phenyl-2,5-bis(2-phenyl-3-benzothienyl)-3,4-diphenylsilacyclopentadiene,
1-tertiarybutyl-1-phenyl-2,5-di(2-benzothiazolyl)-3,4-diphenylsilacyclopentadiene,
1-tertiarybutyl-1-phenyl-2,5-di(2-benzoxazolyl)-3,4-diphenylsilacyclopentadiene,
1-tertiarybutyl-1-phenyl-2,5-bis(5-methyl-2-benzoxazolyl)-3,4diphenylsilacyclopentadiene,
1-tertiarybutyl-1-phenyl-2,5-bis(5-phenyl-2-benzoxazolyl)-3,4-diphenylsilacyclopentadiene,
1-tertiarybutyl-1-phenyl-2,5-bis(5-methyl-2-benzoxazolyl)-3,4
1-tertiarybutyl-1-phenyl-2,5-bis(5-phenyl-2-benzothiazolyl)-3,4-diphenylsilacyclopentadiene,
1-tertiarybutyl-1-phenyl-2,5-di(2-benzofuranyl)-3,4-diphenylsilacyclopentadiene,
1-tertiarybutyl-1-phenyl-2,5-di(3-benzofuranyl)-3,4-diphenylsilacyclopentadiene,
1-tertiarybutyl-1-phenyl-2,5-di(2-benzothienyl)-3,4-diphenylsilacyclopentadiene,
1-tertiarybutyl-1-phenyl-2,5-di(3,4-difluorophenyl)-3,4-diphenylsilacyclopentadiene,
1-tertiarybutyl-1-phenyl-2,5-di(3,4,5-trifluorophenyl)-3,4-diphenylsflacyclopentadiene and
1-tertiarybutyl-1-phenyl-2,5-di(2,3,4,5,6-pentafluorophenyl)-3,4-diphenylsilacyclopentadiene.

Example 306
Synthesis of 1,1-dimethyl-2,5-diphenyl-3,4-bis(3-methylphenyl) silacyclopentadiene 1,1-dimethyl-2,5-diphenyl-3,4-bis(3-methylphenyl) silacyclopentadiene can be synthesized by the method in accordance with Example 1 except that bisphenylethynyldimethylsilane used in Example 1 was substituted with bis(3-methylphenyl)ethynyldimethylsilane.

Example 307~347
Synthesis of various derivatives

As for Examples 307–347, the following various derivatives are synthesized by the similar methods to the method in Example 1 except that bromobenzene used in Example 306 was substituted with corresponding halogenoaryls and that bis(3-methylphenyl)ethynyldimethylsilane was substituted with corresponding silanes:

1,1-dimethyl-2,5-bis(2-methylphenyl)3,4bis(3-methylphenyl)silacyclopentadiene,
1,1-dimethyl-2,5-bis(4-methylphenyl)-3,4-bis(3-methylphenyl)silacyclopentadiene,
1,1-dimethyl-2,5-bis(2-ethylphenyl)-3,4-bis(3-methylphenyl)silacyclopentadiene,
1,1-dimethyl-2,5-bis(3-ethylphenyl)-3,4-bis(3-methylphenyl)silacyclopentadiene,
1,1-dimethyl-2,5-bis(4-ethylphenyl)-3,4-bis(3-methylphenyl)silacyclopentadiene,
1,1-dimethyl-2,5-bis(2-tertiarybutylphenyl)-3,4-bis(3-methylphenyl) silacyclopentadiene,
1,1-dimethyl-2,5-bis(3-tertiarybutylphenyl)-3,4-bis(3-methylphenyl) silacyclopentadiene,
1,1-dimethyl-2,5-bis(4-tertiaiybutylphenyl)-3,4-bis(3-methylphenyl) silacyclopentadiene,
1,1-dimethyl-2,5-bis(2-methylphenyl)-3,4-bis(3-methylphenyl)silacyclopentadiene,
1,1-dimethyl-2,5-bis(3-methylphenyl)-3,4-bis(3-methylphenyl)silacyclopentadiene,
1,1-dimethyl-2,5-bis(4-methylphenyl)-3,4-bis(3-methylphenyl)silacyclopentadiene,
1,1-dimethyl-2,5-bis(2-biphenyl)-3,4-bis(3-methylphenyl) silacyclopentadiene,
1,1-dimethyl-2,5-bis(3-biphenyl)-3,4-bis(3-methylphenyl) silacyclopentadiene,
1,1-dimethyl-2,5-bis(4-biphenyl)-3,4-bis(1-methylphenyl) silacyclopentadiene,
1,1-dimethyl-2,5-bis(2-trifluoromethylphenyl)-3,4-bis(3-methylphenyl) silacyclopentadiene,
1,1-dimethyl-2,5-bis(3-trifluoromethylphenyl)-3,4-bis(3-methylphenyl) silacyclopentadiene,
1,1-dimethyl-2,5-bis(4-trifluoromethylphenyl)-3,4-bis(3-methylphenyl) silacyclopentadiene,
1,1-dimethyl-2,5-bis(2-fluorophenyl)-3,4-bis(3-methylphenyl)silacyclopentadiene,
1,1-dimethyl-2,5-bis(3-fluorophenyl)-3,4-bis(3-methylphenyl)silacyclopentadiene,
1,1-dimethyl-2,5-bis(4-fluorophenyl)-3,4-bis(3-methylphenyl)silacyclopentadiene,
1,1-dimethyl-2,5-bis(2-methoxyphenyl)-3,4-bis(3-methylphenyl)silacyclopentadiene,
1,1-dimethyl-2,5-bis(3-methoxyphenyl)-3,4-bis(3-methylphenyl)silacyclopentadiene,
1,1-dimethyl-2,5-bis(4-methoxyphenyl)-3,4bis(3-methylphenyl)silacyclopentadiene,
1,1-dimethyl-2,5-bis(2-cyanophenyl)-3,4-bis(3-methylphenyl)silacyclopentadiene,
1,1-dimethyl-2,5-bis(3-cyanophenyl)-3,4-bis(3-methylphenyl)silacyclopentadiene,
1,1-dimethyl-2,5-bis(4-cyanophenyl)-3,4-bis(3-methylphenyl)silacyclopentadiene,
1,1-dimethyl-2,5-bis{2-(2-benzoxazolyl)phenyl}-3,4-bis(3-methylphenyl) silacyclopentadiene,
1,1-dimethyl-2,5-bis{3-(2-benzoxazolyl)phenyl}-3,4-bis(3-methylphenyl) silacyclopentadiene,
1,1-dimethyl-2,5-bis{4-(2-benzoxazolyl)phenyl}-3,4-bis(3-methylphenyl) silacyclopentadiene,
1,1-dimethyl-2,5-bis{2-(2-benzothiazolyl)phenyl}-3,4-bis(3-methylphenyl) silacyclopentadiene,
1,1-dimethyl-2,5-bis{3-(2-benzothiazolyl)phenyl}-3,4-bis(3-methylphenyl) silacyclopentadiene,
1,1-dimethyl-2,5-bis{4-(2-benzothiazolyl)phenyl}-3,4-bis(3-methylphenyl) silacyclopentadiene,
1,1-dimethyl-2,5-bis{2-(5-methyl-2-benzoxazolyl)phenyl}-3,4-bis(3-methylphenyl) silacyclopentadiene,
1,1-dimethyl-2,5-bis{3-(5-methyl-2-benzoxazolyl)phenyl}-3,4-bis(3-methylphenyl) silacyclopentadiene,
1,1-dimethyl-2,5-bis{4-(5-methyl-2-benzoxazolyl)phenyl}-3,4-bis(3-methylphenyl) silacyclopentadiene,
1,1-dimethyl-2,5-di(1-naphthyl)-3,4-bis(3-methylphenyl) silacyclopentadiene,
1,1-dimethyl-2,5-di(2-methyl-1-naphthyl)-3,4-bis(3-methylphenyl)silacyclopentadiene,
1,1-dimethyl-2,5-di(2-methoxy-1-naphthyl)-3,4-bis(3-methylphenyl)silacyclopentadiene,
1,1-dimethyl-2,5-di(2-naphthyl)-3,4-bis(3-methylphenyl) silacyclopentadiene,
1,1-dimethyl-2,5-di(6-methoxy-2-naphthyl)-3,4-bis(3-methylphenyl)silacyclopentadiene,
1,1-dimethyl-2,5-di(7-methoxy-2-naphthyl)-3,4-bis(3-methylphenyl)silacyclopentadiene,
1,1-dimethyl-2,5-di(2-benzothienyl)-3,4-bis(3-methylphenyl)silacyclopentadiene,
1,1-dimethyl-2,5-di(3-benzothienyl)-3,4-bis(3-methylphenyl)silacyclopentadiene,
1,1-dimethyl-2,5-bis(3-methyl-2-benzothienyl)-3,4-bis(3-methylphenyl)silacyclopentadiene,
1,1-dimethyl-2,5-bis(3-phenyl-2-benzothienyl)-3,4-bis(3-methylphenyl)silacyclopentadiene,
1,1-dimethyl-2,5-bis(2-methyl-3-benzothienyl)-3,4-bis(3-methylphenyl)silacyclopentadiene,
1,1-dimethyl-2,5-bis(2-phenyl-3-benzothienyl)-3,4-bis(3-methylphenyl)silacyclopentadiene,
1,1-dimethyl-2,5-di(2-benzothiazolyl)-3,4-bis(3-methylphenyl)silacyclopentadiene,
1,1-dimethyl-2,5-di(2-benzoxazolyl)-3,4-bis(3-methylphenyl)silacyclopentadiene,
1,1-dimethyl-2,5-bis(5-methyl-2-benzoxazolyl)-3,4-bis(3-methylphenyl)silacyclopentadiene,
1,1-dimethyl-2,5-bis(5-phenyl-2-benzoxazolyl)-3,4-bis(3-methylphenyl)silacyclopentadiene,
1,1-dimethyl-2,5-bis(5-methyl-2-benzothiazolyl)-3,4-bis(3-methylphenyl)silacyclopentadiene,
1,1-dimethyl-2,5-bis(5-phenyl-2-benzothiazolyl)-3,4-bis(3-methylphenyl)silacyclopentadiene,
1,1-dimethyl-2,5-di(2-benzofuranyl)-3,4-bis(3-methylphenyl)silacyclopentadiene,
1,1-dimethyl-2,5-di(3-benzofuranyl)-3,4-bis(3-methylphenyl)silacyclopentadiene,
1,1-dimethyl-2,5-(2-benzothienyl)-3,4-bis(3-methylphenyl) silacyclopentadiene,
1,1-dimethyl-2,5-bis(3,4-difluorophenyl)-3,4-bis(3-methylphenyl)silacyclopentadiene,
1,1-dimethyl-2,5-bis(3,4,5-trifluorophenyl)-3,4-bis(3-methylphenyl)silacyclopentadiene and
1,1-dimethyl-2,5-bis(2,3,4,5,6-pentafluorophenyl)-3,4-bis(3-methylphenyl) silacyclopentadiene.

Example 348

Synthesis of 1,1-dimethyl-2,3-di(2-pyridyl)-4,5-diphenylsilacyclopentadiene

After substituting inside of a 50 ml two-necked flask containing 2.56 g of naphthalene with argon gas, 140 mg of lithium and 15 ml of THF are added. After stirring for 4 hours, 1.3 g of silane derivative which being synthesized according to Example 1 is added dropwise. It was cooled to 0° C. after 10 minutes, 2.75 g of tertiary-butyl diphenyl silyl chloride is added and stirred for 20 minutes, and then 5.05 g of tetramethylethylenediamine complex of zinc chloride is added. The reaction temperature is returned to the room temperature, and 1.9 g of 2-bromopyridine and 175 mg of bistriphenylphosphine dichloropalladium are added and refluxed for 16 hours. After filtering the deposited solid, the reaction solution is concentrated. 1N hydrochloric acid and diethyl ether are added to the solution obtained, and it is extracted into an aqueous layer. The aqueous layer is rendered to alkaline with an aqueous sodium hydroxide solution, extracted with diethyl ether and washed with water, thereafter dried with sodium sulfate and concentrated. The obtained concentrated solution is recrystallized from a mixed solvent of hexane and ethyl acetate, to obtain 1.3 g of 1,1-dimethyl-2,3-di(2-pryidyl)4,5-diphenyl silacyclopentadiene. The NMR determination results of the obtained compound are described as follows:

$^1$HNMR(CHCl$_3$) δ=0.59(s,6H), 6.50(d,2H), 6.89(m,6H), 7.09(m,6H), 7.20(h,2H), 8.5(m,2H)

Example 349

Synthesis of 1,1-dimethyl-2,3-di(3-pyridyl)-4,5-diphenylsilacyclopentadiene 1,1-dimethyl-2,3-di(3-pyridyl)-4,5-diphenylsilacyclopentadiene was synthesized by the method in accordance with Example 348 except that 2-bromopyridine used in Example 348 was substituted with 3-bromopyridine. The yield was 33 mole %. The NMR determination results are described as follows:

$^1$HNMR(CHCl$_3$) δ=0.50(s,6H), 6.75–6.80(m,4H), 6.95–7.06(m,8H), 7.06–7.12(m,2H), 8.25–8.35(m,4H)

Example 350~383

Synthesis of various derivatives

The following various derivatives can be synthesized by the similar methods to the method in Example 348 except that 2-bromopyridine used in Example 348 was substituted with corresponding halogenoaryls.

1,1-dimethyl-2,5-di(4-pyridyl)-3,4-diphenylsilacyclopentadiene,
1,1-dimethyl-2,5-di(1-isoquinolyl)-3,4-diphenylsflacyclopentadiene,
1,1-dimethyl-2,5-di(2-isoquinolyl)-3,4-diphenylsilacyclopentadiene,
1,1-dimethyl-2,5-di(3-isoquinolyl)-3,4-diphenylsilacyclopentadiene,
1,1-dimethyl-2,5-di(4-isoquinolyl)-3,4-diphenylsilacyclopentadiene,
1,1-dimethyl-2,5-di(5-isoquinolyl)-3,4-diphenylsilacyclopentadiene,
1,1-dimethyl-2,5-di(6-isoquinolyl)-3,4-diphenylsilacyclopentadiene,
1,1-dimethyl-2,5-di(7-isoquinolyl)-3,4-diphenylsilacyclopentadiene,
1,1-dimethyl-2,5-di(8-isoquinolyl)-3,4-diphenylsilacyclopentadiene,
1,1-dimethyl-2,5-di(2-pyrimidyl)-3,4-diphenylsilacyclopentadiene,
1,1-dimethyl-2,5-di(5-pyrimidyl)-3,4-diphenylsilacyclopentadiene,
1,1-dimethyl-2,5-dipyrazyl-3,4-diphenylsilacyclopentadiene,
1,1-dimethyl-2,5-di(3-pyridazyl)-3,4-diphenylsilacyclopentadiene,
1,1-dimethyl-2,5-di(3-isoquinolyl)-3,4-diphenylsilacyclopentadiene,
1,1-dimethyl-2,5-di(4-isoquinolyl)-3,4-diphenylsilacyclopentadiene,
1,1-dimethyl-2,5-di(2-quinoxalyl)-3,4-diphenylsilacyclopentadiene,
1,1-dimethyl-2,5-di(2-quinazolyl)-3,4-diphenylsilacyclopentadiene,
1,1-dimethyl-2,5-di(3-cinnolyl)-3,4-diphenylsilacyclopentadiene,
1,1-dimethyl-2,5-di(9-acrydyl)-3,4-diphenylsilacyclopentadiene,
1,1-dimethyl-2,5-bis(2,3,5,6-tetrafluoro-4-pyridyl)-3,4diphenylsilacyclopentadiene,
1,1-dimethyl-2,5-bis(6-methyl-3-pyridyl)-3,4-diphenylsilacyclopentadiene,
1,1-dimethyl-2,5-bis(6-phenyl-3-pyridyl)-3,4-diphenylsilacyclopentadiene,
1,1-dimethyl-2,5-bis(6-trimethylsilyl-3-pyridyl)-3,4-diphenylsilacyclopentadiene,
1,1-dimethyl-2,5-bis(6-tertiarybutyl-3-pyridyl)-3,4-diphenylsilacyclopentadiene,
1,1-dimethyl-2,5-bis(6-trimethylsilylmethyl-3-pyridyl)3,4-diphenylsilacyclopentadiene,
1,1-dimethyl-2,5-bis{6-(1-naphthyl)-3-pyridyl}-3,4-diphenylsilacyclopentadiene,
1,1-dimethyl-2,5-bis{6-(2-naphthyl)-3-pyridyl}-3,4-diphenylsilacyclopentadiene,
1,1-dimethyl-2,5-bis(6-methyl-2-pyridyl)-3,4-diphenylsilacyclopentadiene,
1,1-dimethyl-2,5-bis(6-phenyl-2-pyridyl)-3,4-diphenylsilacyclopentadiene,
1,1-dimethyl-2,5-bis(6-trimethylsilyl-2-pyridyl)-3,4-diphenylsilacyclopentadiene,
1,1-dimethyl-2,5-bis(6-tertiarybutyl-2-pyridyl)-3,4-diphenylsilacyclopentadiene,
1,1-dimethyl-2,5-bis(6-trimethylsilylmethyl-2-pyridyl)-3,4-diphenylsilacyclopentadiene,
1,1-dimethyl-2,5-bis{6-(1-naphthyl)-2-pyridyl}-3,4-diphenylsilacyclopentadiene,
1,1-dimethyl-2,5-bis{6-(2-naphthyl)-2-pyridyl}-3,4-diphenylsilacyclopentadiene, Example 384~417

Synthesis of various derivatives

As for Example 384–417, the following various derivatives can be synthesized by the similar methods to the method in Example 348 except that 2-bromopyridine used in Example 348 was substituted with corresponding halogenoaryls and that diphenyl ethynyldimethylsilane was substituted with corresponding silanes:

1,1-diethyl-2,5-di(4pyridyl)-3,4-diphenylsilacyclopentadiene,
1,1-diethyl-2,5-di(1-isoquinolyl)-3,4-diphenylsilacyclopentadiene,
1,1-diethyl-2,5-di(2-quinolyl)-3,4-diphenylsilacyclopentadiene,
1,1-diethyl-2,5-di(3-quinolyl)-3,4-diphenylsilacyclopentadiene,
1,1-diethyl-2,5-di(4-quinolyl)-3,4-diphenylsilacyclopentadiene,
1,1-diethyl-2,5-di(5-quinolyl)-3,4-diphenylsilacyclopentadiene,
1,1-diethyl-2,5-di(6-quinolyl)-3,4-&phenylsilacyclopentadiene,
1,1-diethyl-2,5-di(7-quinolyl)-3,4-diphenylsilacyclopentadiene,
1,1-diethyl-2,5-di(8-quinolyl)-3,4-diphenylsilacyclopentadiene,
1,1-diethyl-2,5-di(2-pyrimidyl)-3,4-diphenylsilacyclopentadiene,
1,1-diethyl-2,5-di(5-pyrimidyl)-3,4-diphenylsilacyclopentadiene,
1,1-diethyl-2,5-dipyrazyl-3,4-diphenylsilacyclopentadiene, 1,1-diethyl-2,5-di(3-pyridyl)-3,4-diphenylsilacyclopentadiene,
1,1-diethyl-2,5-di(3-isoquinolyl)-3,4-diphenylsilacyclopentadiene,
1,1-diethyl-2,5-di(4-isoquinolyl)-3,4-diphenylsilacyclopentadiene,
1,1-diethyl-2,5-di(2-quinoxalinyl)-3,4-diphenylsilacyclopentadiene,
1,1-diethyl-2,5-di(2-quinazolinyl)-3,4-diphenylsilacyclopentadiene,
1,1-diethyl-2,5-di(3-cinnolinyl)-3,4-diphenylsilacyclopentadiene,
1,1-diethyl-2,5-di(9-acrydinyl)-3,4-diphenylsilacyclopentadiene,
1,1-diethyl-2,5-bis(2,3,5,6-tetrafluoro-4-pyridyl)-3,4-diphenylsilacyclopentadiene,
1,1-diethyl-2,5-bis(6-methyl-3-pyridyl)-3,4-diphenylsilacyclopentadiene,
1,1-diethyl-2,5-bis(6-phenyl-3-pyridyl)-3,4-diphenylsilacyclopentadiene
1,1-diethyl-2,5-bis(6-trimethylsilyl-3-pyridyl)-3,4-diphenylsilacyclopentadiene,
1,1-diethyl-2,5-bis(6-tertiarybutyl-3-pyridyl)3,4-diphenylsilacyclopentadiene,
1,1-diethyl-2,5-bis(6-trimethylsilylmethyl-3-pyridyl)-3,4-diphenylsilacyclopentadiene,
1,1-diethyl-2,5-bis{6-(1-naphthyl)-3-pyridyl}-3,4-diphenylsilacyclopentadiene,
1,1-diethyl-2,5-bis{6-(2-naphthyl)-3-pyridyl}-3,4-diphenylsilacyclopentadiene,
1,1-diethyl-2,5-bis(6-methyl-2-pyridyl)-3,4-diphenylsilacyclopentadiene,
1,1-diethyl-2,5-bis(6-phenyl-2-pyridyl)-3,4-diphenylsilacyclopentadiene,
1,1-diethyl-2,5-bis(6-trimethylsilyl-2-pyridyl)-3,4-diphenylsilacyclopentadiene,
1,1-diethyl-2,5-bis(6-tertiarybutyl-2-pyridyl)-3,4-diphenylsilacyclopentadiene,
1,1-diethyl-2,5-bis(6-trimethylsilylmethyl-2-pyridyl)-3,4-diphenylsilacyclopentadiene,
1,1-diethyl-2,5-bis{6-(1-naphthyl)-2-pyridyl}-3,4-diphenylsilacyclopentadiene,
1,1-diethyl-2,5-bis{6-(2-naphthyl)-2-pyridyl}-3,4-diphenylsilacyclopentadiene.

Example 418~451
Synthesis of various derivatives
As for Examples 418–451, the following various derivatives can be synthesized by the similar methods to the method in Example 348 except that 2-bromopyridine used in Example 348 was substituted with corresponding halogenoaryls and that diphenylethynyldimethylsilane was substituted with corresponding silanes:
1,1-diphenyl-2,5-di(4-pyridyl)-3,4-diphenylsilacyclopentadiene,
1,1-diphenyl-2,5-di(1-isoquinolyl)-3,4-diphenylsilacyclopentadiene,
1,1-diphenyl-2,5-di(2-quinolyl)-3,4-diphenylsilacyclopentadiene,
1,1-diphenyl-2,5-di(3-quinolyl)-3,4-diphenylsilacyclopentadiene,
1,1-diphenyl-2,5-di(4-quinolyl)-3,4-diphenylsilacyclopentadiene,
1,1-diphenyl-2,5-di(5-quinolyl)-3,4-diphenylsilacyclopentadiene,
1,1-diphenyl-2,5-di(6-quinolyl)-3,4-diphenylsilacyclopentadiene,
1,1-diphenyl-2,5-di(7-quinolyl)-3,4-diphenylsilacyclopentadiene,
1,1-diphenyl-2,5-di(8-quinolyl)-3,4-diphenylsilacyclopentadiene,
1,1-diphenyl-2,5-di(2-pyridyl)-3,4-diphenylsilacyclopentadiene,
1,1-diphenyl-2,5-di(5-pyridyl)-3,4-diphenylsilacyclopentadiene,
1,1-diphenyl-2,5-dipyrazyl-3,4-diphenylsilacyclopentadiene,
1,1-diphenyl-2,5-di(3-pyridyl)-3,4-diphenylsilacyclopentadiene,
1,1-diphenyl-2,5-di(3-isoquinolyl)-3,4-diphenylsilacyclopentadiene,
1,1-diphenyl-2,5-di(4-isoquinolyl)-3,4-diphenylsilacyclopentadiene,
1,1-diphenyl-2,5-di(2-quinoxalyl)-3,4-diphenylsilacyclopentadiene,
1,1-diphenyl-2,5-di(2-quinazolyl)-3,4-diphenylsilacyclopentadiene,
1,1-diphenyl-2,5-di(3-cinnolyl)-3,4-diphenylsilacyclopentadiene,
1,1-diphenyl-2,5-di(9-acrydyl)-3,4-diphenylsilacyclopentadiene,
1,1-diphenyl-2,5-bis(2,3,5,6-tetrafluoro-4-pyridyl)-3,4-diphenylsilacyclopentadiene,
1,1-diphenyl-2,5-bis(6-methyl-3-pyridyl)-3,4-diphenylsilacyclopentadiene,
1,1-diphenyl-2,5-bis(6-phenyl-3-pyridyl)-3,4-diphenylsilacyclopentadiene,
1,1-diphenyl-2,5-bis(6-trimethylsilyl-3-pyridyl)-3,4-diphenylsilacyclopentadiene,
1,1-diphenyl-2,5-bis(6-tertiarybutyl-3-pyridyl)-3,4-diphenylsilacyclopentadiene,
1,1-diphenyl-2,5-bis(6-tertiarybutyl-3-pyridyl)-3,4-diphenylsilacyclopentadiene,
1,1-diphenyl-2,5-bis{6-(1naphthyl)-2-pyridyl}-3,4-diphenylsilacyclopentadiene,
1,1-diphenyl-2,5-bis{6-(2-naphthyl)-2-pyridyl}-3,4-diphenylsilacyclopentadiene,
1,1-diphenyl-2,5-bis(6-methyl-2-pyridyl)-3,4-diphenylsilacyclopentadiene,
1,1-diphenyl-2,5-bis(6-phenyl-2-pyridyl)-3,4-diphenylsilacyclopentadiene,
1,1-diphenyl-2,5-bis(6-trimethylsilyl-2-pyridyl)-3,4-diphenylsilacyclopentadiene,
1,1-diphenyl-2,5-bis(6-tertiarybuthyl-2-pyridyl)-3,4-diphenylsilacyclopentadiene,
1,1-diphenyl-2,5-bis(6-trimethylsilylmethyl-2-pyridyl)-3,4-diphenylsilacyclopentadiene,
1,1-diphenyl-2,5-bis {6-(1-naphthyl)-2-pyridyl}-3,4-diphenylsilacyclopentadiene,
1,1-diphenyl-2,5-bis {6-(2-naphthyl)-2-pyridyl}-3,4-diphenylsilacyclopentadiene.

Example 452~485
Synthesis of various derivatives
As for Examples 452–485, the following various derivatives can be synthesized by the similar methods to the method in Example 348 except that 2-bromopyridine used in Example 348 was substituted with corresponding halogenoaryls and that diphenylethynyldimethylsilane was substituted with corresponding silanes:
1-ethyl-1-methyl-2,5-di(4-pyridyl)-3,4-diphenylsilacyclopentadiene,
1-ethyl-1-methyl-2,5-di(1-isoquinolyl)-3,4-diphenylsilacyclopentadiene,
1-ethyl-1-methyl-2,5-di(2-quinolyl)-3,4-diphenylsilacyclopentadiene,
1-ethyl-1-methyl-2,5-di(3-quinolyl)-3,4-diphenylsilacyclopentadiene, 1-ethyl-1-methyl-2,5-di(4-quinolyl)-3,4-diphenylsilacyclopentadiene,
1-ethyl-1-methyl-2,5-di(5-quinolyl)-3,4-diphenylsilacyclopentadiene,
1-ethyl-1-methyl-2,5-di(6-quinolyl)-3,4-diphenylsilacyclopentadiene,
1-ethyl-1-methyl-2,5-di(7-quinolyl)-3,4-diphenylsilacyclopentadiene,
1-ethyl-1-methyl-2,5-di(8-quinolyl)-3,4-diphenylsilacyclopentadiene,
1-ethyl-1-methyl-2,5-di(2-pyrimidyl)-3,4-diphenylsilacyclopentadiene,
1-ethyl-1-methyl-2,5-di(5-pyrimidyl)-3,4-diphenylsilacyclopentadiene,
1-ethyl-1-methyl-2,5-dipyradyl-3,4-diphenylsilacyclopentadiene,
1-ethyl-1-methyl-2,5-di(3-pyridyl)-3,4-diphenylsilacyclopentadiene,
1-ethyl-1-methyl-2,5-di(3-isoquinolyl)-3,4-diphenylsilacyclopentadiene,
1-ethyl-1-methyl-2,5-di(4-isoquinolyl)-3,4-diphenylsilacyclopentadiene,
1-ethyl-1-methyl-2,5-di(2-quinoxalyl)-3,4-diphenylsilacyclopentadiene,
1-ethyl-1-methyl-2,5-di(2-quinazolyl)-3,4diphenylsilacyclopentadiene,
1-ethyl-1-methyl-2,5-di(32-cinnolyl)-3,4-diphenylsilacyclopentadiene,
1-ethyl-1-methyl-2,5-di(9-acrydyl)-3,4-diphenylsilacyclopentadiene,
1-ethyl-1-methyl-2,5-bis(2,3,5,6-tetrafluoro-4-pyridyl)-3,4-diphenylsilacyclopentadiene,
1-ethyl-1-methyl-2,5-bis(6-methyl-3-pyridyl-3,4-diphenylsilacyclopentadiene,
1-ethyl-1-methyl-2,5-bis(6-phenyl-3-pyridyl)-3,4-diphenylsilacyclopentadiene,
1-ethyl-1-methyl-2,5-bis(6-trimethylsilyl-3-pyridyl)-3,4-diphenylsilacyclopentadiene,
1-ethyl-1-methyl-2,5-bis(6-tertiarybutyl-3-pyridyl)-3,4-diphenylsilacyclopentadiene,
1-ethyl-1-methyl-2,5-bis(6-trimethylsilylmethyl-3-pyridyl)-3,4-diphenylsilacyclopentadiene,
1-ethyl-1-methyl-2,5-bis{6-(1-naphthyl)-3-pyridyl}-3,4-diphenylsilacyclopentadiene,
1-ethyl-1-methyl-2,5-bis{6-(2-naphthyl)-3-pyridyl}-3,4-diphenylsilacyclopentadiene,
1-ethyl-1-methyl-2,5-bis(6-methyl-2-pyridyl)-3,4-diphenylsilacyclopentadiene,
1-ethyl-1-methyl-2,5-bis(6-phenyl-2-pyridyl)-3,4-diphenylsilacyclopentadiene,
1-ethyl-1-methyl-2,5-bis(6-trimethylsilyl-2-pyridyl)-3,4-diphenylsilacyclopentadiene,
1-ethyl-1-methyl-2,5-bis(6-tertiarybutyl-2-pyridyl)-3,4-diphenylsilacyclopentadiene,
1-ethyl-1-methyl-2,5-bis(6-trimethylsilylmethyl-2-pyridyl)-3,4-diphenylsilacyclopentadiene,
1-ethyl-1-methyl-2,5-bis{6-(1-naphthyl)-2-pyridyl}-3,4-diphenylsilacyclopentadiene,
1-ethyl-1-methyl-2,5-bis{6-(2-naphthyl)-2-pyridyl}-3,4-diphenylsilacyclopentadiene.

Example 486~519
Synthesis of various derivatives

As for Examples 486–519, the following various derivatives can be synthesized by the similar methods to the method in Example 348 except that 2-bromopyridine used in Example 348 was substituted with corresponding halogenoaryls and that diphenylethynyldimethylsilane was substituted with corresponding silanes:

1-tertiarybutyl-1-phenyl-2,5-di(4-pyridyl)-3,4-diphenylsilacyclopentadiene,
1-tertiarybutyl-1-phenyl-2,5-di(1-isoquinolyl)-3,4-diphenylsilacyclopentadiene,
1-tertiarybutyl-1-phenyl-2,5-di(2-quinolyl)-3,4-diphenylsilacyclopentadiene,
1-tertiarybutyl-1-phenyl-2,5-di(3-quinolyl)-3,4-diphenylsilacyclopentadiene,
1-tertiarybutyl-1-phenyl-2,5-di(4-quinolyl)-3,4-diphenylsilacyclopentadiene,
1-tertiarybutyl-1-phenyl-2,5-di(5-quinolyl)-3,4-diphenylsilacyclopentadiene,
1-tertiarybutyl-1-phenyl-2,5-di(6-quinolyl)-3,4-diphenylsilacyclopentadiene,
1-tertiarybutyl-1-phenyl-2,5-di(7-quinolyl)-3,4-diphenylsilacyclopentadiene,
1-tertiarybutyl-1-phenyl-2,5-di(8-quinolyl)-3,4-diphenylsilacyclopentadiene,
1-tertiarybutyl-1-phenyl-2,5-di(2-pyrimidyl)-3,4-diphenylsilacyclopentadiene,
1-tertiarybutyl-1-phenyl-2,5-di(5-pyrimidyl)-3,4-diphenylsilacyclopentadiene,
1-tertiarybutyl-1-phenyl-2,5-dipyradinyl-3,4-diphenylsilacyclopentadiene,
1-tertiarybutyl-1-phenyl-2,5-di(3-pyridyl)-3,4-diphenylsilacyclopentadiene,
1-tertiarybutyl-1-phenyl-2,5-di(3-isoquinolyl)-3,4diphenylsilacyclopentadiene,
1-tertiarybutyl-1-phenyl-2,5-di(4-isoquinolyl)-3,4-diphenylsilacyclopentadiene,
1-tertiarybutyl-1-phenyl-2,5-di(2-quinoxalyl)-3,4-diphenylsilacyclopentadiene,
1-tertiarybutyl-1-phenyl-2,5-di(2-quinazolyl)-3,4-diphenylsilacyclopentadiene,
1-tertiarybutyl-1-phenyl-2,5-di(3-cinnolyl)-3,4-diphenylsilacyclopentadiene,
1-tertiarybutyl-1-phenyl-2,5-di(9-acrydyl)-3,4-diphenylsilacyclopentadiene,
1-tertiarybutyl-1-phenyl-2,5-bis(2,3,5,6-tetrafluoro-4-pyridyl)-3,4-diphenylsilacyclopentadiene,
1-tertiarybutyl-1-phenyl-2,5-bis(6-methyl-3-pyridyl)-3,4-diphenylsilacyclopentadiene,
1-tertiarybutyl-1-phenyl-2,5-bis(6-phenyl-3-pyridyl)-3,4-diphenylsilacyclopentadiene,
1-tertiarybutyl-1-phenyl-2,5-bis(6-trimethylsilyl-3-pyridyl)-3,4-diphenylsilacyclopentadiene,
1-tertiarybutyl-1-phenyl-2,5-bis(6-tertiarybuthyl-3-pyridyl)-3,4-diphenylsilacyclopentadiene,
1-tertiarybutyl-1-phenyl-2,5-bis(6-trimethylsilylmethyl-3-pyridyl)-3,4-diphenylsilacyclopentadiene,
1-tertiarybutyl-1-phenyl-2,5-bis{6-(1-naphtyl)-3-pyridyl}-3,4-diphenylsilacyclopentadiene,
1-tertiarybutyl-1-phenyl-2,5-bis{6-(2-naphtyl)3-pyridyl}-3,4-diphenylsilacyclopentadiene,
1-tertiarybutyl-1-phenyl-2,5-bis(6-methyl-2-pyridyl)-3,4-diphenylsilacyclopentadiene,
1-tertiarybutyl-1-phenyl-2,5-bis(6-phenyl-2-pyridyl)-3,4-diphenylsilacyclopentadiene,
1-tertiarybutyl-1-phenyl-2,5-bis(6-trimethylsilyl-2-pyridyl)-3,4-diphenylsilacyclopentadiene,
1-tertiarybutyl-1-phenyl-2,5-bis(6-tertiarybuthyl-2-pyridyl)-3,4-diphenylsilacyclopentadiene,
1-tertiarybutyl-1-phenyl-2,5-bis(6-trimethylsilylmethyl-2-pyridyl)-3,4-diphenylsilacyclopentadiene,
1-tertiarybutyl-1-phenyl-2,5-bis{6-(1-naphthyl)-2-pyridyl}-3,4-diphenylsilacyclopentadiene,
1-tertiarybutyl-1-phenyl-2,5-bis{6-(2-naphthyl)-2-pyridyl}-3,4-diphenylsilacyclopentadiene.

Example 520
Synthesis of 5,5'-dimethyl-1,1,1',1'-tetraethyl-3,3',4,4'-tetraphenyl-2,2'-bicyclopentadiene To 20 ml of a solution containing 0.73 g of 5,5'-dibromo-1,1,1',1'-tetraethyl-3,3',4,4'-tetraphenyl-2,2'-bicyclopentadiene dissolved in diethyl ether, 4 ml of 1N methyl lithium solution in diethyl ether is added under a nitrogen atmosphereat −78° C. After stirring for 1 hour, 10 ml of a solution containing 0.4 g of dimethyl iodide in diethyl ether is added dropwise and stirred at the room temperature for one night. Water is added to the solution and the solution is extracted with diethyl ether. Furthermore, the ether layer is washed with water, thereafter dried with magnesium sulfate and concentrated. After purifying the obtained concentrated solution by means of a column chromatography, recrystallization from a mixed solvent of hexane and ethyl acetate is carried out, to obtain 5,5'-dimethyl-1,1,1',1'-tetraethyl-3,3',4,4'-tetraphenyl-2,2'-bicyclopentadiene. It is in form of light yellow neddle crystals.

Example 521
Synthesis of 1,2-bis(1-methyl-2,3,4,5-tetraphenylsilacyclopentadienyl)ethane 1,2-bis(1-methyl-2,3,4,5-tetraphenylsilacyclopentadienyl)ethane can be synthesized by the method in accordance with Example 1 except that bisphenyl-ethynyldimethylsilane used in Example 1 was substituted with 1,2-bis{bis(phenyl-ethynyl)methylsilyl}ethane.

Example 522~544
Synthesis of various derivatives

As for Examples 522–544, the following various derivatives can be synthesized by the similar methods to the method in Example 1 except that bromobenzene used in Example 521 was substituted with corresponding halogenoaryls:

1,2-bis{1-methyl-2,5-bis(2-methylphenyl)-3,4-diphenylsilacyclopentadienyl}ethane,
1,2-bis{1-methyl-2,5-bis(3-methylphenyl)-3,4-diphenylsilacyclopentadienyl}ethane,
1,2-bis{1-methyl-2,5-bis(4-methylphenyl)-3,4-diphenylsilacyclopentadienyl}ethane,
1,2-bis{1-methyl-2,5-bis(2-fluorophenyl)-3,4-diphenylsilacyclopentadienyl}ethane,
1,2-bis{1-methyl-2,5-bis(3-fluorophenyl)-3,4-diphenylsilacyclopentadienyl}ethane,
1,2-bis{1-methyl-2,5-bis(4-fluorophenyl)-3,4-diphenylsilacyclopentadienyl}ethane,
1,2-bis{1-methyl-2,5-bis(2-methoxyphenyl)-3,4-diphenylsilacyclopentadienyl}ethane,
1,2-bis{1-methyl-2,5-bis(3-methoxyphenyl)-3,4-diphenylsilacyclopentadienyl}ethane,
1,2-bis{1-methyl-2,5-bis(4methoxyphenyl)-3,4-diphenylsilacyclopentadienyl}ethane,
1,2-bis{1-methyl-2,5-bis(2-cyanophenyl)-3,4-diphenylsilacyclopentadienyl}ethane,
1,2-bis{1-methyl-2,5-bis(3-cyanophenyl)-3,4-diphenylsilacyclopentadienyl}ethane,
1,2-bis{1-methyl-2,5-bis(4-cyanophenyl)3,4-diphenylsilacyclopentadienyl}ethane,
1,2-bis{1-methyl-2,5-di(2-biphenyl)-3,4-diphenylsilacyclopentadienyl}ethane,
1,2-bis{1-methyl-2,5-di(3-biphenyl)-3,4-diphenylsilacyclopentadienyl}ethane,
1,2-bis{1-methyl-2,5-di(4-biphenyl)-3,4-diphenylsilacyclopentadienyl}ethane,
1,2-bis{1-methyl-2,5-di(1-naphthyl)-3,4diphenylsilacyclopentadienyl}ethane,
1,2-bis{1-methyl-2,5-di(2-naphthyl)-3,4-diphenylsilacyclopentadienyl}ethane,
1,2-bis{1-methyl-2,5-bis(3,4-difluorophenyl)-3,4-diphenylsilacyclopentadienyl}ethane,
1,2-bis{1-methyl-2,5-bis(3,4,5-trifluorophenyl)-3,4-diphenylsilacyclopentadienyl}ethane,
1,2-bis{1-methyl-2,5-bis(2,3,4,5,6-pentafluorophenyl)-3,4-diphenylsilacyclopentadienyl}ethane,
1,2-bis{1-methyl-2,5-bis(2-trifuoromethylphenyl)-3,4-diphenylsilacyclopentadienyl}ethane,
1,2-bis{1-methyl-2,5-bis(3-trifluoromethylphenyl)-3,4-diphenylsilacyclopentadienyl}ethane and
1,2-bis{1-methyl-2,5-bis(4-trifluoromethylphenyl)-3,4-diphenylsilacyclopentadienyl}ethane.

Example 545
Synthesis of 1,2-bis{1-methyl-2,5-di(2-pyridyl)-3,4-diphenylsilacyclopentadienyl}ethane 1,2-bis{1-methyl-2,5-di(2-pyridyl)-3,4-diphenylsilacyclopentadienyl}ethane was synthesized by the method in accordance with Example 348 except that bisphenylethynyldimethylsilane used in Example 348 was substituted with 1,2-bis{bis(phenylethynyl)methylsilyl}ethane.

Example 546~570
Synthesis of various derivatives

As for Examples 546–570, the following various derivatives can be synthesized by the similar methods to the method in Example 545 except that 2-bromopyridine was substituted with corresponding halogenoaryls:

1,2-bis{1-methyl-2,5-di(3-pyridyl)-3,4-diphenylsilacyclopentadienyl}ethane,
1,2-bis{1-methyl-2,5-di(4-pyridyl)-3,4-diphenylsilacyclopentadienyl}ethane,
1,2-bis{1-methyl-2,5-di(2-quinolyl)-3,4-diphenylsilacyclopentadienyl}ethane,
1,2-bis{1-methyl-2,5-di(3-quinolyl)-3,4-diphenylsilacyclopentadienyl}ethane,
1,2-bis{1-methyl-2,5-di(4-quinolyl)-3,4diphenylsilacyclopentadienyl}ethane,
1,2-bis{1-methyl-2,5-di(5-quinolyl)-3,4-diphenylsilacyclopentadienyl}ethane,
1,2-bis{1-methyl-2,5-di(6-quinolyl)-3,4-diphenylsilacyclopentadienyl}ethane,
1,2-bis{1-methyl-2,5-di(7-quinolyl)-3,4-diphenylsilacyclopentadienyl}ethane,
1,2-bis{1-methyl-2,5-di(8-quinolyl)-3,4-diphenylsilacyclopentadienyl}ethane,
1,2-bis{1-methyl-2,5-di(1-isoquinolyl)-3,4-diphenylsilacyclopentadienyl}ethane,
1,2-bis{1-methyl-2,5-bis(5-methyl-2-pyridyl)-3,4-diphenylsilacyclopentadienyl}ethane,
1,2-bis{1-methyl-2,5-bis(5-phenyl-2-pyridyl)3,4-diphenylsilacyclopentadienyl}ethane.
1,2-bis{1-methyl-2,5-bis(6-methyl-3-pyridyl)-3,4-diphenylsilacyclopentadienyl}ethane,
1,2-bis{1-methyl-2,5-bis(6-phenyl-3-pyridyl)-3,4-diphenylsilacyclopentadienyl}ethane,
1,2-bis{1-methyl-2,5-bis(2,3,5,6-tetrafluoro-4-pyridyl)-3,4-diphenylsilacyclopentadienyl}ethane,
1,2-bis{1-methyl-2,5-di(2-pyrimidyl)-3,4-diphenylsilacyclopentadienyl}ethane,
1,2-bis{1-methyl-2,5-di(5-pyrimidyl)-3,4diphenylsilacyclopentadienyl}ethane,
1,2-bis(1-methyl-2,5-dipyradyl-3,4-diphenylsilacyclopentadienyl)ethane, 1,2-bis{1-methyl-2,5-di(3-pyridyl)-3,4-diphenylsilacyclopentadienyl}ethane,
1,2-bis{1-methyl-2,5-di(3-isoquinolyl)-3,4-diphenylsilacyclopentadienyl}ethane,
1,2-bis{1-methyl-2,5-di(4-isoquinolyl)-3,4diphenylsilacyclopentadienyl}ethane,
1,2-bis{1-methyl-2,5-di(2-quinoxalyl)-3,4-diphenylsilacyclopentadienyl}ethane,
1,2-bis{1-methyl-2,5-di(2-quinazolyl)-3,4-diphenylsilacyclopentadienyl}ethane,
1,2-bis{1-methyl-2,5-di(3-cinnolyl)-3,4-diphenylsilacyclopentadienyl}ethane,
1,2-bis{1-methyl-2,5-di(9-acrydyl)-3,4-diphenylsilacyclopentadienyl}ethane.

Example 571
Synthesis of 9,9-di(1-naphthyl)dibenzosilol

To 10 ml of a solution containing 0.62 g of 2,2'-dibromobiphenyl dissolved in diethyl ether, 5 ml of 1.6N normal butyl lithium solution in hexane was added drop wise at 0° C. After stirring for 1 hour, 10 ml of a solution containing 0.51 g of di(1-naphthyl)dichlorosilane in diethyl ether was refluxed for one day. After the solution was cooled, water was added to it. The solution was extracted with diethyl ether, thereafter dried with magnesiumsulphate and concentrated the solution of diethyl ether. After purifying the obtained concentrated solution by means of a column chromatography, distilled and recrystallization from ethanol, to obtained 800 mg of 9.9-di(1-naphthyl)dibenzosilol.

Example 572~598
Synthesis of various derivatives

As for Examples 572–598, the following various derivatives can be synthesized by the similar methods to the method in Example 571 except that di(1-naphthyl) dichlorosilane used in Example 571 was substituted with corresponding silanes:
9,9-di(2-naphthyl)dibenzosilol,
9,9-bis(2-methyl-1-naphthyl)dibenzosilol,
9,9-di(2-quinolyl)dibenzosilol,
9,9-di(3-quinolyl)dibenzosilol,
9,9-di(4-quinolyl)dibenzosilol,
9,9-di(5-quinolyl)dibenzosilol,
9,9-di(6-quinolyl)dibenzosilol,
9,9-di(7-quinolyl)dibenzosilol,
9,9-di(8-quinolyl)dibenzosilol,
9,9-di(2-biphenyl)dibenzosilol,
9,9-di(3-biphenyl)dibenzosilol,
9,9-di(4-biphenyl)dibenzosilol,
9,9-bis(4'-fluoro-4-biphenyl)dibenzosilol,
9,9-dibenzoxazolyldibenzosilol,
9,9-dibenzothiazolyldibenzosilol,
9-phenyl-9-(2-naphthyl)dibenzosilol,
9-phenyl-9-(1-naphthyl)dibenzosilol,
9-phenyl-9-(4-biphenyl)dibenzosilol,
9-phenyl-9-(3-quinolyl)dibenzosilol,
9-(4-biphenyl)-9-(2-naphthyl)dibenzosilol,
9-(4-biphenyl)-9-(1-naphthyl)dibenzosilol,
9-(4-biphenyl)-9-(3-quinolyl)dibenzosilol,
9-(4-biphenyl)-9-(3-tolyl)dibenzosilol,
9-(1-naphtyl)-9-(2-naphthyl)dibenzosilol,
9-(4-fluorophenyl)-9-(1-naphthyl)dibenzosilol,
9-(3,4-difluorophenyl)-9-(2-naphthyl)dibenzosilol,
9-(3,4,5-trifuorophenyl)-9-(2-naphthyl)dibenzosilol.

Example 599
Synthesis of 2,7-ditertiary-butyl-9,9-di(1-naphthyl) dibenzosilol 2,7-Ditertiary-butyl-9,9-di(1-naphthyl) dibenzosilol can be synthesized by the similar method to the method in Example 571 except that 2,2'-dibromobiphenyl used in Example 571 was substituted by 2,2'-dibromo4,4'-ditertiary-butylbiphenyl.

Application Example 1

A substrate (made by Tokyo Sanyo Shinku Co. Ltd.) which was obtained by coating indium tin oxide (ITO) on a glass substrate of 25 mm×75 mm×1.1 mm at the thickness of 50 nm by means of vacuum evaporation was used as a transparent supporting substrate. The transparent supporting substrate was fixed to a substrate holder of a commercially available vacuum evaporator (made be Shinku Kiko Co., Ltd.), TPD was added into a quartz crucible, 1,3-di(9-anthryl)-2-(9-carbazolylmethyl)-propane (AnCz) was added into an another crucible, the compound obtained in Example 349 (PSP) was added into an another crucible, and then a pressure in a vacuum tank was decreased to $1\times10^{-4}$ Pa.

The crucible containing TPD was heated and vacuum evaporated, to obtain the film thickness of 50 nm. Then, the crucible containing AnCz was heated and vacuum evaporated, to obtain the film thickness of 20 nm. Finally, the crucible containing PSP was heated and vacuum evaporated, to obtain the film thickness of 50 nm. The vacuum evaporation rates were from 0.1 to 0.2 nm/sec.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 5 V was applied to the obtained element by using the ITO electrode as an anode and the mixed electrode of magnesium and silver as a cathode, electric current of about 30 mA/cm$^2$ was flown to obtain green luminescence of 1100 cd/m$^2$.

Comparative Example 1

An element was made by the similar method to Application Example 1 except that the silacyclopentadiene derivative used in Application Example 1 was substituted by the compound expressed by the following Chem. 37. Once direct voltage of 13 V was applied to the obtained element, electric current of 10 mA/cm$^2$ was flown to obtain green luminescence of about 80 cd/m$^2$.

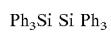

Ph$_3$Si Si Ph$_3$

Comparative Example 2

An element was made by the similar method to Application Example except that the silacyclopentadiene derivative used in Application Example 1 was substituted by the compound expressed by the following formula XXIII. Once direct voltage of 8 V was applied to the obtained element, electric current of 70 mA/cm$^2$ was flown to obtain green luminescence of 1300 cd/m$^2$.

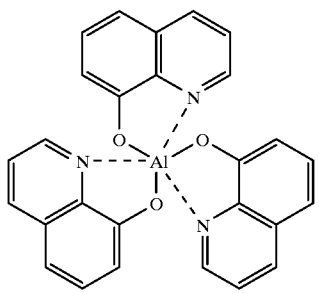

(XXIII)

Application Example 2

A substrate which was obtained by coating ITO on a glass substrate of 25 mm×75 mm×1.1 mm at the thickness of 50 mn by means of vacuum evaporation was used as a transparent supporting substrate. The transparent supporting substrate was fixed to a commercially available spinner (made by Kyoei Semiconductor Co. Ltd.), and a solution containing 50 parts by weight of polyvinyl carbazole, 50 parts by weight of silacyclopentadiene derivative obtained in Example 348 and 1 part by weight of coumarine 6 (Kodak) in toluene was coated at 5000 rpm. Thereafter, the substrate was dried at 50° C. under a decreased pressure of $10^{-1}$ Pa, and then fixed to a substrate holder of a vacuum evaporater.

Thereafter, a pressure in a vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 9 V was applied to the obtained element by using the ITO electrode as an anode and the mixed electrode of magnesium and silver as a cathode, electric current of about 100 mA/cm$^2$ was flown to obtain green luminescence of 1000 cd/m$^2$.

Application Example 3

The substrate used in Application Example 1 was fixed to a substrate holder, then TPD was added into a quartz crucible, the compound obtained in Example 349 was added in an another crucible, and DCM (Kodak) was added in a still another crucible, and a pressure in a vacuum tank was decreased to $1\times10^{-4}$ Pa.

The crucible containing TPD was heated and vacuum evaporated to obtain a film thickness of 50 nm. Then, the crucibles containing the above-mentioned compound and DCM respectively were heated and vacuum co-evaporated to obtain a film thickness of 50 nm. At that time, the concentration of DCM was controlled to 1% by weight of the above-mentioned compound. Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 5 V was applied to the obtained element by using the ITO electrode as an anode and the mixed electrode of magnesium and silver as a cathode, electric current of about 30 mA/cm$^2$ was flown to obtain reddish orange luminescence of 1200 cd/m$^2$.

Application Example 4

A substrate (made by Tokyo Sanyo Shinku Co. Ltd.) which was obtained by coating ITO on a glass substrate of 25 mm×75 mm×1.1 mm at the thickness of 50 nm by means of vacuum evaporation was used as a transparent supporting substrate. The transparent supporting substrate was fixed to a substrate holder of a commercially available vacuum evaporator (made be Shinku Kiko Co. Ltd.), TPD was added into a quartz crucible, 1-allyl-1,2,3,4,5-pentaphenyl silacyclopentadiene (APS) was added into an another crucible, and then a pressure in a vacuum tank was decreased to $1\times10^{-4}$ Pa.

The crucible containing TPD was heated and vacuum evaporated, to obtain the film thickness of 50 nm. Then, the crucible containing ATS was heated and vacuum evaporated, to obtain the film thickness of 50 nm. The vacuum evaporation rates were from 0.1 to 0.2 nm/sec.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 17 V was applied to the obtained element by using the ITO electrode as an anode and the mixed electrode of magnesium and silver as a cathode, electric current of about 100 mA/cm$^2$ was flown to obtain green luminescence of 600 cd/m$^2$. Luminescent wavelength was 503 nm.

Application Example 5

An element was made by the similar method to Example 4 except that APS used therein was substituted by 1-hydroxy-1,2,3,4,5-pentaphenyl silacyclopentadiene. Once direct voltage of 17 V was applied to the obtained element, electric current of about 300 mA/cm$^2$ was flown to obtain green luminescence of about 500 cd/m$^2$. Luminescent wavelength was 516 nm.

Application Example 6

An element was made by the similar method to Example 4 except that APS used therein was substituted by 1,1-dimethyl-2,5-bis(3-methylphenyl)-3,4-diphenyl silacyclopentadiene. Once direct voltage of 13 V was applied to the obtained element, electric current of about 800 mA/cm$^2$ was flown to obtain greenish blue luminescence of about 1000 cd/m$^2$. Luminescent wavelength was 488 nm.

Application Example 7

An element was made by the similar method to Example 4 except that APS used therein was substituted by 1,1-dimethyl-2,5-bis(3-trifluoromethylphenyl)-3,4-diphenyl silacyclopentadiene. Once direct voltage of 4 V was applied to the obtained element, electric current was flown to obtain green luminescence.

Application Example 8

An element was made by the similar method to Example 4 except that APS used therein was substituted by 1,1-dimethyl-2,5-bis(3-pyridyl)-3,4-diphenyl silacyclopentadiene. Once direct voltage of 4 V was applied to the obtained element, electric current was flown to obtain green luminescence.

Application Example 9

An element was made by the similar method to Example 4 except that APS used therein was substituted by 1,1-dimethyl-2,5-bis(2-pyridyl)-3,4-diphenyl silacyclopentadiene. Once direct voltage of 9 V was applied to the obtained element, electric current of about 100 mA/cm$^2$ was flown to obtain green luminescence of about 500 cd/m$^2$.

Application Example 10

An element was made by the similar method to Example 4 except that APS used therein was substituted by 1-methyl-1-phenyl-2,5-bis(3-pyridyl)-3,4-diphenyl silacyclopentadiene. Once direct voltage of 10 V was applied to the obtained element, electric current of about 300 mA/cm2 was flown to obtain green luminescence of about 900 cd/m2.

Application Example 11

An element was made by the similar method to Example 4 except that APS used therein was substituted by 1,1-diisopropyl-2,5-bis(3-pyridyl)-3,4-diphenyl silacyclopentadiene. Once direct voltage of 11 V was applied to the obtained element, electric current of about 100 mA/cm$^2$ was flown to obtain green luminescence of about 200 cd/m$^2$.

Application Example 12

An element was made by the similar method to Example 4 except that APS used therein was substituted by 1,1-dimethyl-2,5-bis(2-thienyl)-3,4-diphenyl silacyclopentadiene. Once direct voltage of 3.5 V was applied to the obtained element, electric current of about 30 mA/cm$^2$ was flown to obtain green luminescence of about 30 cd/m$^2$.

Application Example 13

An element was made by the similar method to Example 4 except that APS used therein was substituted by 1,1-dlisopropyl-2,5-bis(2-thienyl)-3,4-diphenyl silacyclopentadiene. Once direct voltage of 3.5 V was applied to the obtained element, electric current was flown to obtain yellowish green luminescence.

Application Example 14

An element was made by the similar method to Example 4 except that APS used therein was substituted by 1,1-dimethyl-2,5-bis(5-tertiary-butyldiphenylsilyl-2-thienyl)-3,4-diphenyl silacyclopentadiene. Once direct voltage of 12.5 V was applied to the obtained element, electric current of about 600 mA/cm$^2$ was flown to obtain yellowish green luminescence of about 2000 cd/m$^2$. Luminescent wavelength was 551 nm.

Application Example 15

An element was made by the similar method to Example 4 except that APS used therein was substituted by TTSTT. Once direct voltage of 4 V was applied to the obtained element, electric current of about 10 mA/cm$^2$ was flown to obtain orange luminescence of about 1 cd/m$^2$.

Application Example 16

An element was made by the similar method to Example 4 except that APS used therein was substituted by 9,9'-silaspirobifluorene. Once direct voltage of 13 V was applied to the obtained element, electric current of about 300 mA/cm$^2$ was flown to obtain violet luminescence of about 50 cd/m$^2$. Luminescent spectra were completely agreed with fluorescent spectra of TPD vacuum evaporated film, and luminescent wavelength was 405 nm.

Application Example 17

The transparent supporting substrate used in Example 4 was fixed to a substrate holder of a commercially available vacuum evaporator, TPD was added into a quartz crucible, APS was added into an another crucible, 4,4'-bis(2,2-diphenylvinyl)biphenyl (DPVBi) was added into an another crucible, and then a pressure in a vacuum tank was decreased to 1×10$^{-4}$ Pa The crucible containing TPD was heated and vacuum evaporated, to obtain the film thickness of 50 nm. Thereon, the crucible containing DPVBi was heated and vacuum evaporated, to obtain the film thickness of 20 nm, and thereon the crucible containing ATS was heated and vacuum evaporated, to obtain the film thickness of 50 nm. The vacuum evaporation rates were from 0.1 to 0.2 nm/sec.

Thereafter, the pressure in the vacuum tank was decreased to 2×10$^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nn/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage was applied to the obtained element by using the ITO electrode as an anode and the mixed electrode of magnesium and silver as a cathode, electric current was flown to obtain blue luminescence. Luminescent spectra were completely agreed with fluorescent spectra of DPVBi vacuum evaporated film.

Application Example 18

An element was made by the similar method to Example 17 except that APS used therein was substituted by TTSTT. Once direct voltage of 9.5 V was applied to the obtained element, electric current of about 100 mA/cm$^2$ was flown to obtain blue luminescence.

Application Example 19

An element was made by the similar method to Example 17 except that APS used therein was substituted by 1,1-dimethyl-2,5-bis(3 -fluorophenyl)-3,4-diphenyl silacyclopentadiene. Once direct voltage of 9 V was applied to the obtained element, electric current of about 100 mA/cm$^2$ was flown to obtain blue luminescence.

Application Example 20

An element was made by the similar method to Example 17 except that APS used therein was substituted by 1,1-dimethyl-2,5-bis(3-pyridyl)-3,4-diphenyl silacyclopentadiene. Once direct voltage of 7 V was applied to the obtained element, electric current of about 100 mA/cm² was flown to obtain blue luminescence.

Application Example 21

An element was made by the similar method to Example 17 except that APS used therein was substituted by 1,2-bis (9-methyl-dibenzosilacyclopentadienyl)ethane. Once direct voltage was applied to the obtained element, electric current was flown to obtain blue luminescence.

Application Example 22

The transparent supporting substrate used in Example 4 was fixed to a substrate holder of a commercially available vacuum evaporator, TPD was added into a quartz crucible, TTSTT was added into an another crucible, Alq was added into an another crucible, and then a pressure in a vacuum tank was decreased to $1\times10^{-4}$ Pa.

The crucible containing TPD was heated and vacuum evaporated, to obtain the film thickness of 50 nm. Thereon, the crucibles containing TTSTT and Alq were heated and vacuum evaporated, to obtain the film thicknesses of 50 nm. The vacuum evaporation rate of Alq was from 0.1 to 0.2 nm/sec and that of TTSTT was 1/100 of Alq.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 11 V was applied to the obtained element by using the ITO electrode as an anode and the mixed electrode of magnesium and silver as a cathode, electric current of about 900 mA/cm² was flown to obtain yellowish orange luminescence of about 20000 cd/m².

Application Example 23

An element was made by the similar method to Example 17 except that the vacuum evaporation rate of TTSTT used therein was substituted by 3/100 of Alq. Once direct voltage of 12 V was applied to the obtained element, electric current of about 900 mA/cm² was flown to obtain reddish orange luminescence of about 12000 cd/m². The same reddish orange luminescence from the element was observed after the operation for 300 hours.

Application Example 24

An element was made by the similar method to Example 18 except that TTSTT used therein was substituted by 1,1-diisopropyl-2,5-bis(2-thienyl)-3,4diphenyl silacyclopentadiene. Once direct voltage of 10 V was applied to the obtained element, electric current of about 500 mA/cm² was flown to obtain yellow luminescence of about 8000 cd/m².

Application Example 25

The transparent supporting substrate used in Example 4 was fixed to a substrate holder of a commercially available vacuum evaporator, TTSTT was added into a quartz crucible,. and then a pressure in a vacuum tank was decreased to $1\times10^{-4}$ Pa.

The crucible containing TTSTT was heated and vacuum evaporated for TTSTT, to obtain the film thicknesses of 100 nm. The vacuum evaporation rate was from 0.1 to 0.2 nm/sec.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nim/sec. from an another crucible. Under the conditions described above, a mixed metallic electrode of magnesium and silver was laminated at 200 mn on a luminescent layer by vacuum evaporation to obtain a reference electrode, from which an element is formed.

Once direct voltage was applied to the obtained element by using the ITO electrode as an anode and the mixed electrode of magnesium and silver as a cathode, electric current was flown to obtain reddish orange luminescence.

Application Example 26

The transparent supporting substrate used in Example 4 was fixed to a substrate holder of a commercially available vacuum evaporator, TPD was added into a quartz crucible, TTSTT was added into an another crucible, Alq was added into an another crucible, and then a pressure in a vacuum tank was decreased to $1\times10^{-4}$ Pa.

The crucible containing TPD was heated and vacuum evaporated, to obtain the film thickness of 50 nm. Thereon, the crucible containing TTSTT was heated and vacuum evaporated, to obtain the film thickness of 10 nm, and then the crucible containing Alq was heated and vacuum evaporated, to obtain the film thickness of 20 nm. The vacuum evaporation rates were from 0.1 to 0.2 nm/sec.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage was applied to the obtained element by using the ITO electrode as an anode and the mixed electrode of magnesium and silver as a cathode, electric current was flown to obtain reddish orange luminescence.

Application Example 27

The transparent supporting substrate used in Example 4 was fixed to a commercially available spinner (made by Kyoei Semiconductor Kabushiki Kaisha), and coated with a solution of 50 parts by weight of polyvinyl carbazole and 50 parts by weight of 9,9'-silaspirobifluorene in 1,2-dichloroethane at 5000 rpm. Thereafter, this substrate was dried at 50° C. under a decreased pressure of $10^{-1}$ Pa and then fixed to a holder of the vacuum evaporator.

Thereafter, the pressure in the vacuum tank was decreased to $2\times10^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage of 14 V was applied to the obtained element by using the ITO electrode as an anode and the mixed electrode of magnesium and silver as a cathode, electric current of about 300 mA/cm$^2$ was fown to obtain violet luminescence of about 20 cd/m$^2$.

Application Example 28

An element was made by the similar method to Example 26 except that the solution of 50 parts by weight of polyvinyl carbazole and 50 parts by weight of 9,9'-silaspirobifluorene in 1,2-dichloroethane used in Example 24 was substituted by a solution of 50 parts by weight of polyvinyl carbazole, 50 parts by weight of 9,9'-silaspirobifluorene and 1 part by weight of coumarin 6 (made by KODAK) in 1,2-dichloroethane. Once direct voltage was applied to the obtained element, electric current was flown to obtain green luminescence.

Application Example 29

An element was made by the similar method to Example 28 except that coumarin 6 used therein was substituted by perylene. Once direct voltage was applied to the obtained element, electric current was flown to obtain blue luminescence.

Application Example 30

An element was made by the similar method to Example 28 except that coumarin 6 used therein was substituted by Nile Red. Once direct voltage was applied to the obtained element, electric current was flown to obtain orange luminescence.

Application Example 31

An element was made by the similar method to Example 17 except that DPVBi used therein was substituted by 9,9'-silaspirobifluorene and APS used therein was substituted by Alq. Once direct voltage of 12 V was applied to the obtained element, electric current of about 300 m cm$^2$ was flown to obtain violet luminescence of about 1200 cd/m$^2$. Luminescent spectra were completely agreed with fluorescent spectra of TPD vacuum evaporated film, and luminescent wavelength was 405 nm.

Application Example 32

The transparent supporting substrate used in Example 4 was fixed to a substrate holder of a commercially available vacuum evaporator, 40 parts by weight of TPD was added into a quartz crucible, 60 parts of APS was added into an another crucible, 1 part of coumarin 6 was added into an another crucible, and then a pressure in a vacuum tank was decreased to 1×10$^{-4}$ Pa.

The crucibles were heated and vacuum evaporated, to obtain the film thickness of 100 nm. The vacuum evaporation rates were from 1.0 to 1.2 nm/sec.

Thereafter, the pressure in the vacuum tank was decreased to 2×10$^{-4}$ Pa, then magnesium was vacuum evaporated at the vacuum evaporation rate of from 1.2 to 2.4 nm/sec. from a graphite crucible and simultaneously silver was vacuum evaporated at the vacuum evaporation rate of from 0.1 to 0.2 nm/sec. from an another crucible. Under the conditions described above, a mixed metallic electrode of magnesium and silver was laminated at 200 nm on a luminescent layer by vacuum evaporation to obtain a reference electrode, from which an element is formed.

Once direct voltage was applied to the obtained element by using the ITO electrode as an anode and the mixed electrode of magnesium and silver as a cathode, electric current was flown to obtain green luminescence.

Application Example 33

An element was made by the similar method to Example 17 except that APS used therein was substituted by 1,1-dimethyl-2,5-bis(2-pyridyl)-3,4-diphenyl silacyclopentadiene. Once direct voltage of 4.5 V was applied to the obtained element, electric current of about 7 mA/cm$^2$ was flown to obtain blue luminescence of about 130 cd/m$^2$. Maximum luminescence of the element was above 6000 cd/m$^2$.

Application Example 34

An element was made by the similar method to Example 17 except that DPVBi used therein was substituted by Alq. Once direct voltage of 3 V was applied to the obtained element, electric current of about 1 mA/cm$^2$ was flown to obtain blue luminescence of about 20 cd/m$^2$. Maximum luminescence of the element was above 13000 cd/m$^2$.

Effect of the Invention

The compounds according to the invention are useful as electron-transporting materials for organic EL elements or electrophotography due to superior electron-transporting ability. In the case of using them as organic EL elements, they can emit luminescence with high luminance at a low voltage and have high practical values compared to the elements in which conventional electron-transporting materials being used. By using them, luminescent elements having high efficiency such as full color displays etc. can be made.

The organic electroluminescent elements according to the invention can emit luminescence with high luminance at a low voltage and have high practical values, since they use silacyclopentadiene derivatives which are superior in electron-transporting ability. By using them, luminescent elements having high efficiency such as fill color flat panel displays etc. can be made.

What is claimed is:

1. A silacyclopentadiene derivative expressed by the following formula I

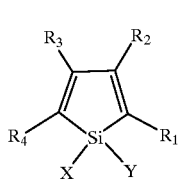

(I)

wherein X and Y denote independently each other saturated or unsaturated hydrocarbon groups with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated ring, and from R$_1$ to R$_4$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radicals, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, sulfinyl radical, sulfonyl radical, sulfanyl radical, silyl radical, carbamoyl radical, aryl radicals, heterocyclic radicals, alkenyl- radicals; alkynyl radicals, nitro radical, formyl radical, nitroso radical, formyloxy radical, isocyano radical, cyanate radical, isocyanate radical, thiocyanate radical, isothiocyanate radical or cyano radical, or they may form a structure of a substituted or unsubstituted condensed ring if they are adjacent, with the proviso that in the case of $R_1$ and $R_4$ being phenyl radicals, X and Y are not alkyl radicals or phenyl radicals; in the case of $R_1$ and $R_4$ being thienyl radicals, X and Y are not monovalent hydrocarbons simultaneousy, and $R_2$ and $R_3$ are not alkyl radicals, aryl radicals, alkenyl radicals or $R_2$ and $R_3$ are not aliphatic radicals to form a ring simultaneously; in the case of $R_1$ and $R_4$ being silyl radicals, $R_2$, $R_3$, X and Y are independent each other and are not monovalent hydrocarbon radicals with from 1 to 6 carbon atoms or hydrogen atom; and in the case of $R_1$ and $R_2$ being condensed to form a benzene ring, X and Y are not alkyl radicals and phenyl radicals.

2. A silacyclopentadiene derivative expressed by the following formula II

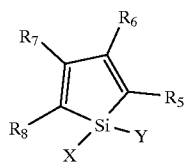

(II)

wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and from $R_5$ to $R_8$ denote independently each other hydrogen, fluorine, chlorine, substituted or unsubstituted alkyl radicals with from 1 to 6 carbon atoms, alkoxy radicals, perfluoroalkyl radicals, perfluoroalkoxy radicals, dialkylamino radicals, diarylamino radicals, silyl radical, aryl radicals, heterocyclic radicals or cyano radical, or they may form a structure of a substituted or unsubstituted condensed ring if they are adjacent, with the proviso that in the case of $R_5$ and $R_6$ being phenyl radicals, X and Y are not alkyl radicals and phenyl radicals; in the case of $R_5$ and $R_8$ being thienyl radicals, X and Y are not monovalent hydrocarbons simultaneously, and $R_6$ and $R_7$ are not alkyl radicals, aryl radicals or alkenyl radicals or $R_6$ and $R_7$ are not aliphatic radicals to form a ring simultaneously; in the case of $R_5$ and $R_8$ being silyl radicals, $R_6$, $R_7$, X and Y are independent each other and are not monovalent hydrocarbon radicals with from 1 to 6 carbon atoms or hydrogen atom; and in the case of $R_5$ and $R_6$ being condensed to form a benzene ring, X and Y are not alkyl radicals and phenyl radicals and halogens.

3. A silacyclopentadiene derivative expressed by the following formula III

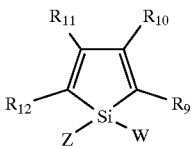

(III)

wherein, Z and W denote independently each other saturated or hydrocarbon radicals with from 1 to 6 carbon atoms, substituted or unsubstituted aryl radicals or substituted or unsubstituted heterocycles, or Z and W are bonded together to form a structure of a saturated ring, and from $R_9$ to $R_{12}$ denote independently each other substituted or unsubstituted alkyl radicals with from 1 to 6 carbon atoms, perfluoroalkyl radicals, diarylamino radicals, silyl radical, aryl radicals or heterocyclic radicals, or they may form a structure of a substituted or unsubstituted condensed ring if they are adjacent, with the proviso that in the case of $R_9$ and $R_{12}$ being phenyl radicals, Z and W are not alkyl radicals and phenyl radicals; in the case of $R_9$ and $R_{12}$ being thienyl radicals, Z and W are not monovalent hydrocarbons simultaneously, and $R_{10}$ and $R_{11}$ are not alkyl radicals or aryl radicals or $R_{10}$ and $R_{11}$ are not aliphatic radicals to form a ring simultaneously; in the case of $R_9$ and $R_{12}$ being silyl radicals, $R_{10}$, $R_{11}$, Z and W are independent each other and are not monovalent hydrocarbon radicals with from 1 to 6 carbon atoms or hydrogen atom; and in the case of $R_9$ and $R_{10}$ being condensed to form a benzene ring, Z and W are not alkyl radicals and phenyl radicals.

4. A silacyclopentadiene derivative expressed by the following formula IV

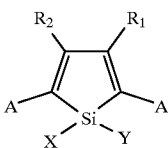

(IV)

wherein, A denotes a zinc halide or a zinc halide complex, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_1$ and $R_2$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, heterocyclic radicals, alkenyl radicals, alkynyl radicals, nitro radical, formyl radical, nitroso radical, formyloxy radical, isocyano radical, cyanate radical, isocyanate radical, thiocyanate radical, isothiocyanate radical or cyano radical, or a structure of a substituted or unsubstituted condensed ring.

5. A silacyclopentadiene derivative expressed by the following formula V

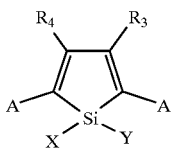

(V)

wherein, A denotes a zinc halide or a zinc halide complex, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_3$ and $R_4$ denote independently each other hydrogen, fluorine, chlorine, substituted or unsubstituted alkyl radicals with from 1 to 6 carbon atoms, alkoxy radicals, perfluoroalkyl radicals, perfluoroalkoxy radicals, dialkylamino radicals, diarylamino radicals, silyl radical, aryl radicals, heterocyclic radicals or cyano radical, or they may form a structure of a substituted or unsubstituted condensed ring.

6. A silacyclopentadiene derivative expressed by the following formula VI

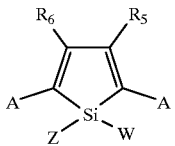

(VI)

wherein, A denotes a zinc halide or a zinc halide complex, Z and W denote independently each other saturated or unsaturated hydrocarbon radicals with from 1 to 6 carbon atoms, substituted or unsubstituted aryl radicals or substituted or unsubstituted heterocycles, or X and Y are bonded together to form a structure of a saturated or unsaturated ring, and from $R_5$ and $R_6$ denote independently each other substituted or unsubstituted allVl radicals with from 1 to 6 carbon atoms, perfluoroalkyl radicals, diarylamino radicals, silyl radical, aryl radicals or heterocyclic radicals, or they may form a structure of a substituted or unsubstituted condensed ring.

7. A process for preparing a silacyclopentadiene derivative according to claim 4, characterized in that an acetylene derivative expressed by the following formula VII:

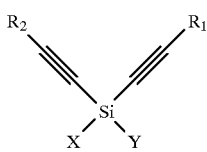

(VII)

wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_1$ and $R_2$ denote independently each other hydrogen, halogens, substituted or unsubstituted alkyl radicals with from 1 to 6 carbon atoms, alkoxy radicals, aryloxy radicals, perfluoroalkyl radicals, perfluoroalkoxy radicals, amino radical, alkylcarbonyl radicals, arylcarbonyl radicals, alkoxycarbonyl radicals, aryloxycarbonyl radicals, azo radical, alkylcarbonyloxy radicals, arylcarbonyloxy radicals, alkoxycarbonyloxy radicals, aryloxycarbonyloxy radicals, sulfinyl radical, sulfonyl radical, sulfanil radical, silyl radical, carbamoyl radical, aryl radicals, heterocyclic radicals, alkenyl radicals, alkynyl radicals, nitro radical, formyl radical, nitroso radical, formyloxy radical, isocyano radical, cyanate radical, isocyanate radical, thiocyanate radical, isothiocyanate radical, cyano radical, or a structure of a substituted or unsubstituted condensed ring is reacted with an alkali metal complex, then with a silane derivative expressed by the following formula VIII:

(VIII)

wherein, X, Y and Z denote independently tertiary butyl radicals or aryl radicals), and thereafter with zinc chloride or a zinc chloride complex.

8. A process for preparing a silacyclopentadiene derivative according to claim 5, characterized in that an acelylene derivative expressed by the following formula IX:

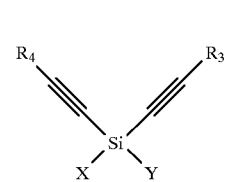

(IX)

wherein, X and Y denote independently each other saturated or unsaturated hydrocarbon radicals with from 1 to 6 carbon atoms, alkoxy radicals, alkenyloxy radicals, alkynyloxy radicals, substituted or unsubstituted aryl radicals or substituted or unsubstituted heterocycles, or X and Y are bonded together to form a structure of a saturated or unsaturated ring, and $R_3$ and $R_4$ denote independently each other hydrogen, fluorine, chlorine, substituted or unsubstituted alkl radicals with from 1 to 6 carbon atoms, alkoxy radicals, perfluoroalkyl radicals, perfluoroalkoxy radicals, dialkylainino radicals, diarylamino radicals, silyl radical, aryl radicals, heterocyclic radicals, cyano radical or a structure of a substituted or unsubstituted condensed ring is reacted with an alkali metal complex, then with a silane derivative expressed by the following formula X:

(X)

wherein, X, Y and Z denote independently tertiary butyl radicals or aryl radicals, and thereafter furthermore with zinc chloride or a zinc chloride complex.

9. A process for preparing a silacyclopentadiene derivative according to claim 6, characterized in that an acelylene derivative expressed by the following formula XI:

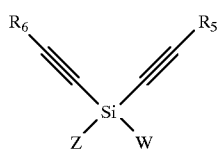

(XI)

wherein, A denotes a zinc halide or a zinc halide complex, X and Y denote independently each other saturated or unsaturated hydrocarbon radicals with from 1 to 6 carbon atoms, substituted or unsubstituted aryl radicals or substituted or unsubstituted heterocycles, or X and Y are bonded together to form a structure of a saturated or unsaturated ring, and from $R_5$ and $R_6$ denote independently each other substituted or unsubstituted alkyl radicals with from 1 to 6 carbon atoms, perfluoroallyl radicals, diarylamino radicals, silyl radical, aryl radicals or heterocyclic radicals, or they may form a structure of a substituted or unsubstituted condensed ring is reacted with an alkali metal complex, then with a silane derivative expressed by the following formula X:

(X)

wherein, X, Y and Z denote independently tertiary butyl radicals or aryl radicals, and thereafter furthermore with zinc chloride or a zinc chloride complex.

10. A process for preparing a silacyclopentadiene derivative, characterized in that a silacyclopentadiene derivative according to claim 7 is reacted with a halide expressed by the following formula XII:

LX (XII)

wherein, X represents chlorine, bromine or iodine, and L denotes a halogen, a saturated or unsaturated hydrocarbon radical with from 1 to 6 carbon atoms, a perfluoroalkyl radical, an alkylcarbonyl radical, an arylcarbonyl radical, an alkoxycarbonyl radical, an aryloxy carbonyl radical, a sulfinyl radical, a sulfonyl radical, a sulfanil radical, a silyl radical, an aryl radical, a heterocyclic radical, an alkenyl radical or an alkynyl.

11. A process for preparing a silacyclopentadiene derivative, characterized in that a silacyclopentadiene derivative according to claim 8 is reacted with a halide expressed by the following formula XIII:

MX (XIII)

wherein, X represents chlorine, bromine or iodine, and M denotes fluorine, chlorine, a saturated or unsaturated hydrocarbon radical with from 1 to 6 carbon atoms, a perfluoroalkyl radical, a silyl radical, an aryl radical or a heterocyclic radical.

12. A process for preparing a silacyclopentadiene derivative, characterized in that a silacyclopentadiene derivative according to claim 9 is reacted with a halide expressed by the following formula XV:

NX (XIV)

wherein, X represents chlorine, bromine or iodine, and N denotes a saturated or unsaturated hydrocarbon radical with from 1 to 6 carbon atoms, a perfluoroalkyl radical, a silyl radical, an aryl radical or a heterocyclic radical.

* * * * *